(12) United States Patent
Choi et al.

(10) Patent No.: US 10,347,841 B2
(45) Date of Patent: Jul. 9, 2019

(54) COMPOUND FOR ORGANIC PHOTOELECTRIC DEVICE AND ORGANIC PHOTOELECTRIC DEVICE IMAGE SENSOR, AND ELECTRONIC DEVICE INCLUDING THE SAME

(71) Applicant: Samsung Electronics Co., Ltd., Suwon-si, Gyeonggi-do (KR)

(72) Inventors: Yeong Suk Choi, Suwon-si (KR); Yong Wan Jin, Seoul (KR); Chang Duk Yang, Ulsan (KR); Gyeongsik Kim, Cheongju-si (KR); Yujin Ahn, Ulsan (KR)

(73) Assignees: Samsung Electronics Co., Ltd., Gyeonggi-do (KR); Unist Academy-Industry Research Corporation, Ulju-Gun Ulsan (KR)

( * ) Notice: Subject to any disclaimer, the term of this patent is extended or adjusted under 35 U.S.C. 154(b) by 29 days.

(21) Appl. No.: 15/253,995

(22) Filed: Sep. 1, 2016

(65) Prior Publication Data

US 2017/0062726 A1  Mar. 2, 2017

(30) Foreign Application Priority Data

Sep. 1, 2015 (KR) .................. 10-2015-0123873

(51) Int. Cl.
*H01L 51/00* (2006.01)
*C07D 333/24* (2006.01)
(Continued)

(52) U.S. Cl.
CPC ........ *H01L 51/0052* (2013.01); *C07C 255/31* (2013.01); *C07D 333/24* (2013.01);
(Continued)

(58) Field of Classification Search
CPC .............. C07C 255/31; C07C 2601/16; C07C 2603/18; C07C 2103/18; C07C 255/09; C07D 333/24; C07D 407/10; C07D 409/10; C07D 493/04; C07D 495/04; H01L 27/307; H01L 51/0052; H01L 51/0068;
(Continued)

(56) References Cited

U.S. PATENT DOCUMENTS 7,018,685 B2    3/2006  Schmidt et al.
2012/0068163 A1*  3/2012  Nagai ............... C08G 61/02
                                            257/40

FOREIGN PATENT DOCUMENTS

CN    102260191     * 11/2011
DE    102015101768  *  8/2016

OTHER PUBLICATIONS

Qing-Xiu Wu et al., "Theoretical studies of the effect of electron-withdrawing dicya group on the electronic and charge-transport properties of fiuorene-thiophene oligomers", Theor Chem Acc, Published Online Feb. 25, 2012, Springer-Verlag 2012.*

(Continued)

*Primary Examiner* — Matthew L Reames
*Assistant Examiner* — Benjamin Tzu-Hung Liu
(74) *Attorney, Agent, or Firm* — Harness, Dickey & Pierce, P.L.C.

(57) ABSTRACT

A compound for an organic photoelectric device includes at least one of a compound represented by Chemical Formula 1, a compound represented by Chemical Formula 2 and a combination thereof.

29 Claims, 7 Drawing Sheets

(51) Int. Cl.
  *H01L 27/30*  (2006.01)
  *C07C 255/49*  (2006.01)
  *C07C 255/31*  (2006.01)
  *H01L 51/44*  (2006.01)

(52) U.S. Cl.
  CPC ........ *H01L 27/307* (2013.01); *H01L 51/0068* (2013.01); *C07C 2601/16* (2017.05); *C07C 2603/18* (2017.05); *H01L 51/447* (2013.01)

(58) Field of Classification Search
  CPC ............... H01L 51/447; H01L 27/1461; H01L 27/14621; H01L 27/14645; H01L 51/4253; H01L 51/441
  See application file for complete search history.

(56) References Cited

OTHER PUBLICATIONS

Qing-Xiu Wu et al., "Theoretical studies of the effect of electron-withdrawing dicyanovinyl group on the electronic and charge-transport properties of fluorene-thiophene oligomers", Theor Chem Acc, Published Online Feb. 25, 2012, Springer-Verlag 2012.

* cited by examiner

COMPOUND FOR ORGANIC PHOTOELECTRIC DEVICE AND ORGANIC PHOTOELECTRIC DEVICE IMAGE SENSOR, AND ELECTRONIC DEVICE INCLUDING THE SAME

CROSS REFERENCE TO RELATED APPLICATION

This application claims priority to and the benefit of Korean Patent Application No. 10-2015-0123873 filed in the Korean Intellectual Property Office on Sep. 1, 2015, the entire contents of which are incorporated herein by reference.

BACKGROUND

1. Field

Example embodiments relate to a compound for an organic photoelectric device, and an organic photoelectric device, an image sensor, and an electronic device including the same.

2. Description of the Related Art

A photoelectric device typically converts light into an electrical signal using photoelectric effects, and may include a photodiode, a phototransistor, etc. The photodetector may be applied to an image sensor, a solar cell, an organic light emitting diode, etc.

An image sensor including a photodiode requires typically high resolution, and thus, a relatively small pixel. At present, a silicon photodiode is widely used, but exhibits deteriorated sensitivity because of a relatively small absorption area due to relatively small pixels. Accordingly, an organic material that is capable of replacing silicon has been researched.

The organic material has a relatively high extinction coefficient and selectively absorbs light in a particular wavelength region depending on a molecular structure, and thus may simultaneously replace a photodiode and a color filter, thereby improving sensitivity and contributing to relatively high integration.

SUMMARY

Example embodiments provide a compound for an organic photoelectric device having improved light absorption properties.

Example embodiments also provide an organic photoelectric device including the compound for an organic photoelectric device.

Example embodiments also provide an image sensor including the organic photoelectric device.

Example embodiments also provide an electronic device including the image sensor.

According to example embodiments, a compound for an organic photoelectric device is selected from at least one of a compound represented by Chemical Formula 1, a compound represented by Chemical Formula 2, and a combination thereof.

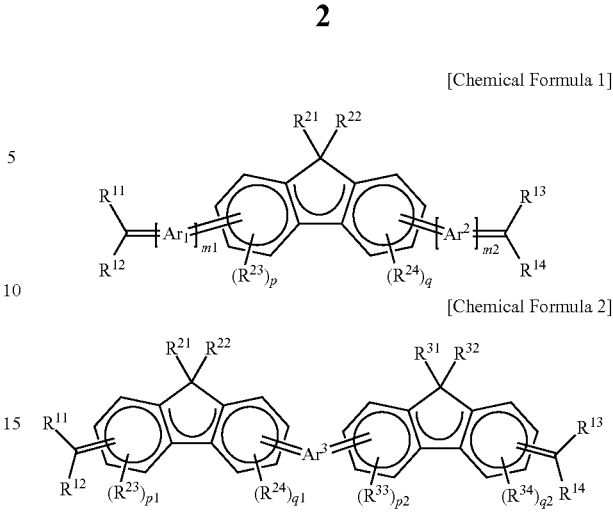

[Chemical Formula 1]

[Chemical Formula 2]

In Chemical Formulae 1 and 2, each of $R^{11}$ to $R^{14}$ are independently one of hydrogen, a chloro group (—Cl), a bromo group (—Br), a substituted or unsubstituted $C_1$ to $C_{10}$ alkyl group, a cyano group (—CN), and a combination thereof, provided that both $R^{11}$ and $R^{12}$ are not hydrogen and both $R^{13}$ and $R^{14}$ are not hydrogen, each of $R^{21}$, $R^{22}$, $R^{31}$, and $R^{32}$ are independently one of hydrogen, a chloro group (—Cl), a bromo group (—Br), a substituted or unsubstituted $C_1$ to $C_{30}$ alkyl group, and a combination thereof or are optionally linked to provide a spiro structure with a fluorene ring, each of $R^{23}$, $R^{24}$, $R^{33}$, and $R^{34}$ are independently one of hydrogen, a chloro group (—Cl), a bromo group (—Br), a substituted or unsubstituted $C_1$ to $C_{10}$ alkyl group, a cyano group (—CN), and a combination thereof, each of $Ar^1$, $Ar^2$, and $Ar^3$ are independently one of a substituted or unsubstituted $C_6$ to $C_{30}$ arylene group, a substituted or unsubstituted $C_3$ to $C_{30}$ heteroarylene group, and a combination thereof, each of p, p1, p2, q, q1, and q2 are independently an integer ranging from 0 to 3, and each of m1 and m2 are independently 0 or 1.

In Chemical Formula 1 or 2, at least one of $R^{11}$ to $R^{14}$ may be a cyano group (—CN). In Chemical Formula 1 or 2, at least two to four of $R^{11}$ to $R^{14}$ may be a cyano group (—CN).

In Chemical Formula 1 or 2, each of $R^{21}$, $R^{22}$, $R^{31}$, and $R^{32}$ may be independently one of a $C_1$ to $C_{30}$ alkyl group substituted with an aryl group and a $C_1$ to $C_{30}$ alkyl group substituted with a cycloalkyl group.

In Chemical Formula 1 or 2, each of $R^{21}$, $R^{22}$, $R^{31}$, and $R^{32}$ may independently be a $C_1$ to $C_{30}$ alkyl group where a methylene group (—($CH_2$)—) that is not adjacent to a fluorene group is replaced by an arylene group or a cycloalkylene group.

In Chemical Formula 1 or 2, each of $Ar^1$, $Ar^2$, and $Ar^3$ may be one of a substituted or unsubstituted phenylene group, a substituted or unsubstituted thiophene group, a substituted or unsubstituted thienothiophene group, and a combination thereof.

The compound represented by Chemical Formula 1 may be a compound represented by one of Chemical Formulae 1-1 to 1-3.

[Chemical Formula 1-1]

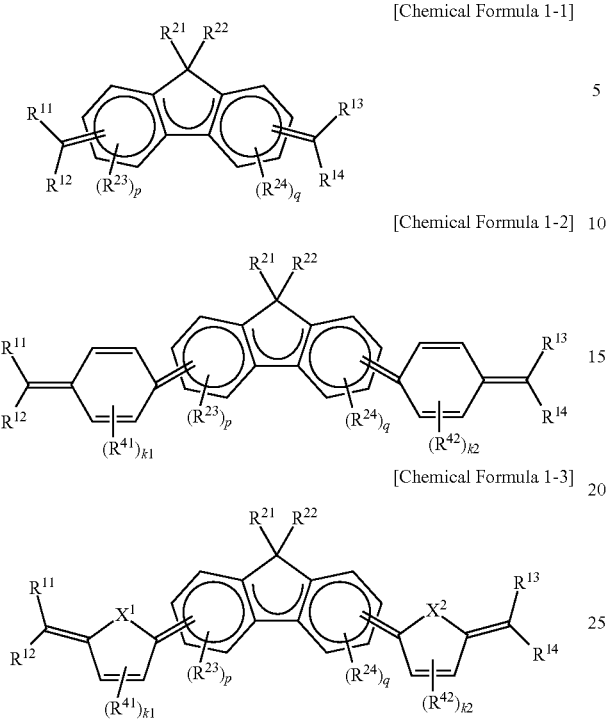

[Chemical Formula 1-2]

[Chemical Formula 1-3]

[Chemical Formula 2-1]

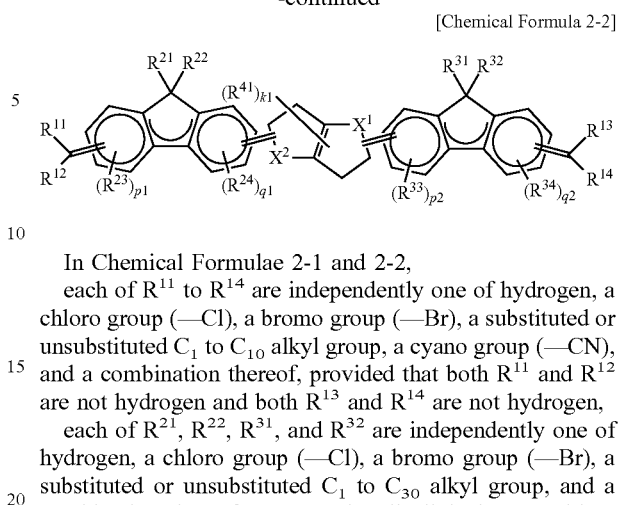

[Chemical Formula 2-2]

In Chemical Formulae 1-1 to 1-3, each of $R^{11}$ to $R^{14}$ are independently one of hydrogen, a chloro group (—Cl), a bromo group (—Br), a substituted or unsubstituted $C_1$ to $C_{10}$ alkyl group, a cyano group (—CN), and a combination thereof, provided that both $R^{11}$ and $R^{12}$ are not hydrogen and both $R^{13}$ and $R^{14}$ are not hydrogen, each of $R^{21}$ and $R^{22}$ are independently one of hydrogen, a chloro group (—Cl), a bromo group (—Br), a substituted or unsubstituted $C_1$ to $C_{30}$ alkyl group, and a combination thereof or are optionally linked to provide a spiro structure with a fluorene ring, each of $R^{23}$, $R^{24}$, $R^{41}$, and $R^{42}$ are independently one of hydrogen, a chloro group (—Cl), a bromo group (—Br), a substituted or unsubstituted $C_1$ to $C_{10}$ alkyl group, a cyano group (—CN), and a combination thereof, each of p and q are integers ranging from 0 to 3, each of k1 and k2 correspond to the number of hydrogen in each aromatic ring, and each of $X^1$ and $X^2$ are independently one of S and O.

In Chemical Formulae 1-1 to 1-3, at least one of $R^{11}$ to $R^{14}$ may be a cyano group (—CN). In Chemical Formulae 1-1 to 1-3, at least two to four of $R^{11}$ to $R^{14}$ may be a cyano group (—CN).

The compound represented by Chemical Formula 2 may be a compound represented by Chemical Formulae 2-1 or Chemical Formula 2-2.

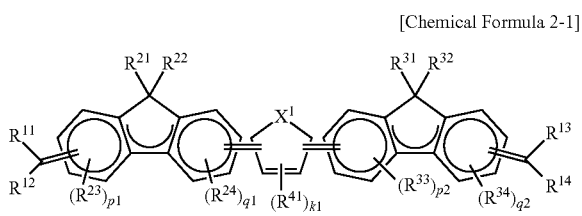

In Chemical Formulae 2-1 and 2-2, each of $R^{11}$ to $R^{14}$ are independently one of hydrogen, a chloro group (—Cl), a bromo group (—Br), a substituted or unsubstituted $C_1$ to $C_{10}$ alkyl group, a cyano group (—CN), and a combination thereof, provided that both $R^{11}$ and $R^{12}$ are not hydrogen and both $R^{13}$ and $R^{14}$ are not hydrogen, each of $R^{21}$, $R^{22}$, $R^{31}$, and $R^{32}$ are independently one of hydrogen, a chloro group (—Cl), a bromo group (—Br), a substituted or unsubstituted $C_1$ to $C_{30}$ alkyl group, and a combination thereof or are optionally linked to provide a spiro structure with a fluorene ring, each of $R^{23}$, $R^{24}$, $R^{33}$, $R^{34}$, and $R^{41}$ are independently one of hydrogen, a chloro group (—Cl), a bromo group (—Br), a substituted or unsubstituted $C_1$ to $C_{10}$ alkyl group, a cyano group (—CN), and a combination thereof, each of p1, p2, q1, and q2 are integers ranging from 0 to 3, k1 corresponds to the number of hydrogen in each aromatic ring, and each of $X^1$ and $X^2$ are independently one of S and O.

In Chemical Formula 2-1 or 2-2, at least one of $R^{11}$ to $R^{14}$ may be a cyano group (—CN). In Chemical Formula 2-1 or 2-2, at least two to four of $R^{11}$ and $R^{14}$ may be a cyano group (—CN).

The compound may have a maximum absorption peak ($\lambda_{max}$) in a wavelength region in a thin film state of about 300 nm to about 720 nm, for example about 300 nm to about 600 nm.

The compound may show a light absorption curve having a full width at half maximum (FWHM) in a thin film state of about 50 nm to about 150 nm.

The compound may be one of a p-type semiconductor compound and an n-type semiconductor compound.

The compound may have a bandgap of about 2.0 eV to about 4.0 eV.

The compound may have a LUMO level of about 2.0 eV to about 4.2 eV.

According to example embodiments, an organic photoelectric device includes a first electrode and a second electrode facing each other, and an active layer between the first electrode and the second electrode and including the compound selected from at least one of the compound represented by Chemical Formula 1, the compound represented by Chemical Formula 2, and a combination thereof.

According to example embodiments, an image sensor includes the organic photoelectric device.

The image sensor may further include a semiconductor substrate integrated with a plurality of first photo-sensing devices configured to sense light in a blue wavelength region, a plurality of second photo-sensing devices configured to sense light in a red wavelength region, and a plurality of third photo-sensing devices configured to sense light in a green wavelength region, wherein the organic photoelectric device may be on the semiconductor substrate and configured to selectively absorb light in a green wavelength region.

The image sensor may include a semiconductor substrate integrated with a plurality of first photo-sensing devices configured to sense light in a blue wavelength region and a plurality of second photo-sensing devices configured to sense light in a red wavelength region, and the organic photoelectric device may be on the semiconductor substrate and configured to selectively absorb light in a green wavelength region.

The image sensor may further include a color filter layer between the semiconductor substrate and the organic photoelectric device, and including a blue filter configured to selectively transmit light in a blue wavelength region and a red filter configured to selectively transmit light in a red wavelength region.

At least two photo-sensing devices selected from the first photo-sensing devices, the second photo-sensing devices and the third photo-sensing devices may be stacked in a vertical direction on the semiconductor substrate.

The organic photoelectric device may be a green photoelectric device, and the green photoelectric device configured to selectively absorb light in a blue wavelength region, a blue photoelectric device configured to selectively absorb light in a blue wavelength region, and a red photoelectric device configured to selectively absorb light in a red wavelength region may be stacked.

According to example embodiments, an electronic device includes the image sensor.

DETAILED DESCRIPTION

Figure 1:
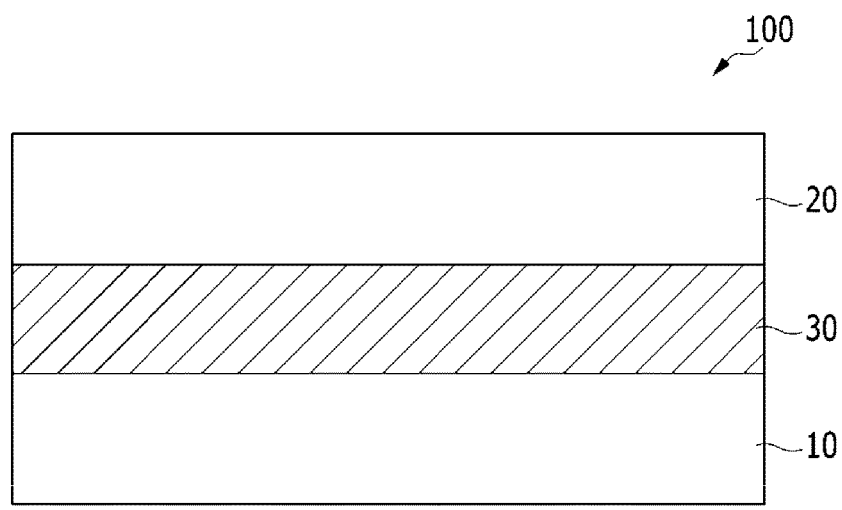
FIG. 1 is a cross-sectional view showing an organic photoelectric device according to example embodiments.

Example embodiments will hereinafter be described in detail, and may be easily performed by those who have common knowledge in the related art. However, this disclosure may be embodied in many different forms and is not to be construed as limited to the example embodiments set forth herein.

As used herein, when specific definition is not otherwise provided, the term "substituted" refers to one substituted with a substituent selected from a halogen atom (Br, Cl or I), a nitro group, a cyano group, an amino group, an azido group, an amidino group, a hydrazino group, a hydrazono group, a carbonyl group, a carbamyl group, a thiol group, a $C_1$ to $C_{20}$ alkyl group, a $C_1$ to $C_{20}$ alkoxy group, a $C_2$ to $C_{20}$ alkenyl group, a $C_2$ to $C_{20}$ alkynyl group, a $C_6$ to $C_{30}$ aryl group, a $C_7$ to $C_{30}$ arylalkyl group, a $C_1$ to $C_{20}$ alkoxy group, a $C_1$ to $C_{20}$ heteroalkyl group, a $C_3$ to $C_{20}$ heteroarylalkyl group, a $C_3$ to $C_{30}$ cycloalkyl group, a $C_3$ to $C_{15}$ cycloalkenyl group, a $C_6$ to $C_{15}$ cycloalkynyl group, a $C_2$ to $C_{20}$ heterocycloalkyl group, and a combination thereof, instead of hydrogen of a compound or a group.

As used herein, when specific definition is not otherwise provided, the term "hetero" refers to one including 1 to 3 heteroatoms selected from N, O, S, P, and Si.

As used herein, when a definition is not otherwise provided, the term "combination thereof" refers to at least two substituents bound to each other by a single bond or a $C_1$ to $C_{10}$ alkylene group, or at least two fused substituents.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numerals throughout the specification.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," etc.) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Hereinafter, a compound for an organic photoelectric device according to example embodiments is described.

A compound for an organic photoelectric device according to example embodiments is selected from a compound represented by Chemical Formula 1, a compound represented by Chemical Formula 2 and a combination thereof.

[Chemical Formula 1]

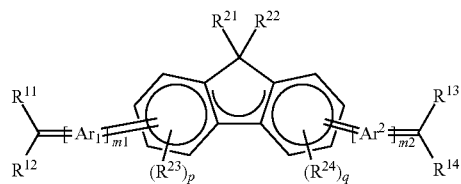

[Chemical Formula 2]

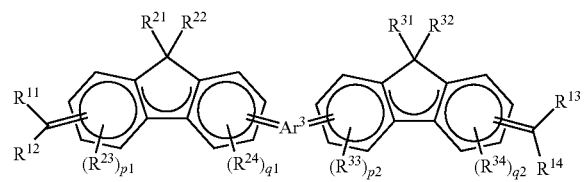

In Chemical Formulae 1 and 2, each of $R^{11}$ to $R^{14}$ are independently one of hydrogen, a chloro group (—Cl), a bromo group (—Br), a substituted or unsubstituted $C_1$ to $C_{10}$ alkyl group, a cyano group (—CN), and a combination thereof, provided that both $R^{11}$ and $R^{12}$ are not hydrogen and both $R^{13}$ and $R^{14}$ are not hydrogen, each of $R^{21}$, $R^{22}$, $R^{31}$, and $R^{32}$ are independently one of hydrogen, a chloro group (—Cl), a bromo group (—Br), a substituted or unsubstituted $C_1$ to $C_{30}$ alkyl group, and a combination thereof or are optionally linked to provide a spiro structure with a fluorene ring, each of $R^{23}$, $R^{24}$, $R^{33}$, and $R^{34}$ are independently one of hydrogen, a chloro group (—Cl), a bromo group (—Br), a substituted or unsubstituted $C_1$ to $C_{10}$ alkyl group, a cyano group (—CN), and a combination thereof, each of $Ar^1$, $Ar^2$, and $Ar^3$ are independently one of a substituted or unsubstituted $C_6$ to $C_{30}$ arylene group, a substituted or unsubstituted $C_3$ to $C_{30}$ heteroarylene group, and a combination thereof, each of p, p1, p2, q, q1, and q2 are independently an integer ranging from 0 to 3, and each of m1 and m2 are independently 0 or 1.

When p, p1, p2, q, q1, and q2 are 2 or 3, a plurality of $R^{21}$, $R^{22}$, $R^{31}$, and $R^{32}$ may be the same or different.

In Chemical Formula 1 or 2, when $R^{11}$ to $R^{14}$ are independently a substituted or unsubstituted $C_1$ to $C_{10}$ alkyl group, the compound represented by Chemical Formula 1 or 2 may be used as a p-type semiconductor compound. In addition, when one of $R^{11}$ to $R^{14}$ in Chemical Formula 1 or 2 is a chloro group (—Cl), a bromo group (—Br), or a cyano group (—CN), the compound may be used as a p-type semiconductor compound.

In Chemical Formula 1 or 2, at least two to four of $R^{11}$ to $R^{14}$ may be a cyano group (—CN). At least one of $R^{11}$ and $R^{12}$ may be a cyano group (—CN) and at least one of $R^{13}$ and $R^{14}$ may be a cyano group (—CN). Herein, the compound represented by Chemical Formula 1 or 2 may be used as an n-type semiconductor compound. The cyano group (—CN) at the terminal end may effectively adjust the HOMO level of the compound represented by Chemical Formula 1 or 2.

The compound represented by Chemical Formula 1 or 2 may be manufactured into a thin film through a deposition process or a solution process. For example, when $R^{21}$ and $R^{22}$ in Chemical Formula 1 or 2 are an alkyl group having greater than or equal to about 7 carbons or a $C_1$ to $C_{30}$ alkyl group substituted with a $C_6$ to $C_{12}$ aryl group or a $C_5$ to $C_{12}$ cycloalkyl group, the compound may be desirably used in the solution process.

In Chemical Formula 1 or 2, $R^{21}$ and $R^{22}$ may independently be a $C_1$ to $C_{30}$ alkyl group where a methylene group (—($CH_2$)—) that is not adjacent to a fluorene group is replaced by a $C_6$ to $C_{12}$ arylene group or a $C_5$ to $C_{12}$ cycloalkylene group.

In Chemical Formulae 1 and 2, $Ar^1$, $Ar^2$, and $Ar^3$ may independently be one of a substituted or unsubstituted phenylene group, a substituted or unsubstituted thiophene group, a substituted or unsubstituted thienothiophene group, and a combination thereof.

In Chemical Formulae 1 and 2, a functional group including a double bond may be bound at the positions 2 and 7 of fluorene. Herein, the energy level (HOMO and LUMO levels) of a compound for an organic photoelectric device may be easily controlled, and thus the absorption intensity of the compound may be increased.

In addition, a compound having a structure linked through a double bond as shown in Chemical Formulae 1 and 2 may have a narrow full width at half maximum (FWHM) in a light absorption curve compared with a compound having a structure linked through a single bond. In other words, the compound may have improved wavelength selectivity.

The compounds represented by Chemical Formulae 1 and 2 overall may form a conjugation structure and thus improve light absorption properties in various wavelength regions.

In Chemical Formulae 1 and 2, $Ar^1$, $Ar^2$, and $Ar^3$ are a 5-membered or 6-membered aromatic ring forming a conjugation structure with the double bond. Herein, the aromatic ring indicates arylene or heteroarylene, and the heteroarylene may contain 1 to 3 heteroatoms (e.g., N, O, S, P, and Si) inside the ring.

When m1 and m2 are 0 in Chemical Formula 1, a compound may have a structure of Chemical Formula 1-1 that a double bond is directly linked to a fluorene structure, and when m1 and m2 is 1, a compound may have a structure that a fluorene structure is linked through a double bond with $Ar^1$ and $Ar^2$ and for example, may be represented by Chemical Formula 1-2 or 1-3.

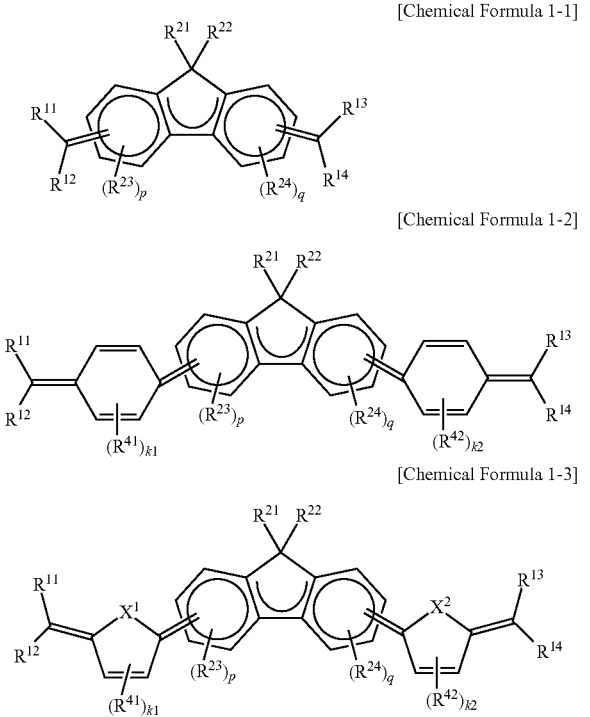

[Chemical Formula 1-1]

[Chemical Formula 1-2]

[Chemical Formula 1-3]

In Chemical Formulae 1-1 to 1-3, each of $R^{11}$ to $R^{14}$ are independently one of hydrogen, a chloro group (—Cl), a bromo group (—Br), a substituted or unsubstituted $C_1$ to $C_{10}$ alkyl group, a cyano group (—CN), and a combination thereof, provided that both $R^{11}$ and $R^{12}$ are not hydrogen and both $R^{13}$ and $R^{14}$ are not hydrogen, each of $R^{21}$ and $R^{22}$ are independently one of hydrogen, a chloro group (—Cl), a bromo group (—Br), a substituted or unsubstituted $C_1$ to $C_{30}$ alkyl group, and a combination thereof or are optionally linked to provide a spiro structure with a fluorene ring, each of $R^{23}$, $R^{24}$, $R^{41}$, and $R^{42}$ are independently one of hydrogen, a chloro group (—Cl), a bromo group (—Br), a substituted or unsubstituted $C_1$ to $C_{10}$ alkyl group, a cyano group (—CN), and a combination thereof, each of k1 and k2 correspond to the number of hydrogen in each aromatic ring, for example an integer ranging from 0 to 4, each of p and q are integers ranging from 0 to 3, and each of $X^1$ and $X^2$ are independently one of S and O.

In Chemical Formulae 1-1 to 1-3, when $R^{11}$ to $R^{14}$ are independently a substituted or unsubstituted $C_1$ to $C_{10}$ alkyl group, the compound of Chemical Formulae 1-1 to 1-3 may be used as a p-type semiconductor compound. In addition, when one of $R^{11}$ to $R^{14}$ in Chemical Formulae 1-1 to 1-3 is a chloro group (—Cl), a bromo group (—Br), or a cyano group (—CN), the compound may be used as a p-type semiconductor compound.

In Chemical Formulae 1-1 to 1-3, at least one of $R^{11}$ to $R^{14}$ may be a cyano group (—CN). At least one of $R^{11}$ and $R^{12}$ may be a cyano group (—CN) and at least one of $R^{13}$ and $R^{14}$ may be a cyano group (—CN). Herein, the compound of Chemical Formula Chemical Formulae 1-1 to 1-3 may be used as an n-type semiconductor compound. The cyano group (—CN) may effectively adjust the HOMO levels of the compounds represented by Chemical Formulae 1-1 to 1-3.

The compounds of Chemical Formulae 1-1 to 1-3 may be formed into a thin film through a deposition process or a solution process. For example, when $R^{21}$ and $R^{22}$ in Chemical Formulae 1-1 to 1-3 are an alkyl group having greater than or equal to about 7 carbons or a $C_1$ to $C_{30}$ alkyl group substituted with a $C_6$ to $C_{12}$ aryl group or a $C_5$ to $C_{12}$ cycloalkyl group, the compound may be used in a solution process.

In Chemical Formulae 1-1 to 1-3, $R^{21}$ and $R^{22}$ may independently be a $C_1$ to $C_{30}$ alkyl group where a methylene group (—(CH$_2$)—) that is not adjacent to a fluorene group is replaced by a $C_6$ to $C_{12}$ arylene group or a $C_5$ to $C_{12}$ cycloalkylene group.

In Chemical Formulae 1-1 to 1-3, a functional group including a double bond may be bound at the positions 2 and 7 of fluorene. Herein, the energy level (HOMO and LUMO levels) of the compound for an organic photoelectric device may be easily controlled, and the absorption intensity of the compound may be increased.

The compound represented by Chemical Formula 2 may be compounds represented by Chemical Formula 2-1 or 2-2.

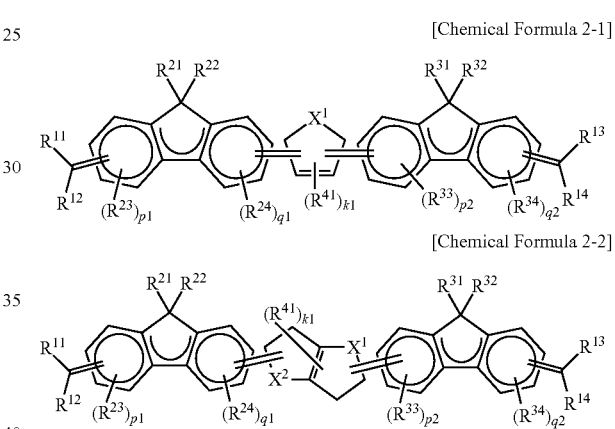

[Chemical Formula 2-1]

[Chemical Formula 2-2]

In Chemical Formulae 2-1 and 2-2, each of $R^{11}$ to $R^{14}$ are independently one of hydrogen, a chloro group (—Cl), a bromo group (—Br), a substituted or unsubstituted $C_1$ to $C_{10}$ alkyl group, a cyano group (—CN), and a combination thereof, provided that both $R^{11}$ and $R^{12}$ are not hydrogen and both $R^{13}$ and $R^{14}$ are not hydrogen, each of $R^{21}$, $R^{22}$, $R^{31}$, and $R^{32}$ are independently one of hydrogen, a chloro group (—Cl), a bromo group (—Br), a substituted or unsubstituted $C_1$ to $C_{30}$ alkyl group, and a combination thereof or are optionally linked to provide a spiro structure with a fluorene ring, each of $R^{23}$, $R^{24}$, $R^{33}$, $R^{34}$, and $R^{41}$ are independently one of hydrogen, a chloro group (—Cl), a bromo group (—Br), a substituted or unsubstituted $C_1$ to $C_{10}$ alkyl group, a cyano group (—CN), and a combination thereof, each of p1, p2, q1, and q2 are integers ranging from 0 to 3, each of k1 corresponds to the number of hydrogen in each aromatic ring, for example an integer ranging from 0 to 4, and each of $X^1$ and $X^2$ are independently one of S and O.

When $R^{11}$ to $R^{14}$ are independently a substituted or unsubstituted $C_1$ to $C_{10}$ alkyl group in Chemical Formulae 2-1 and 2-2, the compounds of Chemical Formulae 2-1 and 2-2 may be used as a p-type semiconductor compound. In addition, when one out of $R^{11}$ to $R^{14}$ in Chemical Formula Chemical Formulae 2-1 and 2-2 is a chloro group (—Cl), a bromo group (—Br), or a cyano group (—CN), the compound may be used as a p-type semiconductor compound.

In Chemical Formulae 2-1 and 2-2, at least one of $R^{11}$ to $R^{14}$ may be a cyano group (—CN). At least one of $R^{11}$ and $R^{12}$ may be a cyano group (—CN) and at least one of $R^{13}$ and $R^{14}$ may be a cyano group (—CN). In this case, the compound may be an n-type semiconductor compound. The cyano group (—CN) may effectively adjust the HOMO levels of the compounds represented by Chemical Formulae 2-1 and 2-2.

The compounds of Chemical Formulae 2-1 and 2-2 may be formed into a thin film through a deposition process or a solution process. For example, when $R^{21}$ and $R^{22}$ in Chemical Formulae 2-1 and 2-2 are an alkyl group having greater than or equal to about 7 or a $C_1$ to $C_{30}$ alkyl group substituted with a $C_6$ to $C_{12}$ aryl group or a $C_5$ to $C_{12}$ cycloalkyl group, the compound may desirably be used in the solution process.

In Chemical Formulae 2-1 and 2-2, $R^{21}$, $R^{22}$, $R^{31}$, and $R^{32}$ may independently be a $C_1$ to $C_{30}$ alkyl group where a methylene group (—CH$_2$—) that is not adjacent to a fluorene group is replaced by a $C_6$ to $C_{12}$ arylene group or a $C_5$ to $C_{12}$ cycloalkylene group.

In Chemical Formulae 2-1 and 2-2, a functional group including a double bond may be bound at the positions 2 and 7 of fluorene. Herein, the energy level (HOMO and LUMO levels) of the compound for an organic photoelectric device may be easily increased, and the absorption intensity of the compound may be increased.

The compound for an organic photoelectric device in a thin film state may efficiently absorb light in various wavelength regions in a UV/Vis absorption spectrum. In example embodiments, the compound for an organic photoelectric device may have a maximum absorption peak ($\lambda_{max}$) in a wavelength region of about 300 nm to about 750 nm, for example about 300 nm to about 720 nm, for example about 300 nm to about 600 nm. The compound for an organic photoelectric device may show a light absorption curve having a full width at half maximum (FWHM) of about 50 nm to about 150 nm, for example about 50 nm to about 100 nm depending on a wavelength, in a thin film state.

The compound for an organic photoelectric device may have a bandgap of about 2.0 eV to about 4.0 eV, for example about 2.3 eV to about 4.0 eV, or about 2.9 eV to about 4.0 eV. The compound has a bandgap within the range and thus may have strong light absorption properties in a particular wavelength region.

The compound for an organic photoelectric device may have a LUMO energy level of about 2.0 eV to 4.2 eV, for example about 2.5 eV to about 4.2 eV or about 2.8 eV to about 4.1 eV. The compound has a LUMO energy level within the range and thus may improve external quantum efficiency (EQE) and effectively adjust the external quantum efficiency depending on a bias applied thereto.

The compound for an organic photoelectric device may be used for an organic photoelectric device or an organic solar cell.

Hereinafter, an organic photoelectric device according to example embodiments is described with reference to drawings.

FIG. 1 is a cross-sectional view showing an organic photoelectric device according to example embodiments.

Referring to FIG. 1, an organic photoelectric device 100 according to example embodiments includes a first electrode 10 and a second electrode 20, and an active layer 30 between the first electrode 10 and the second electrode 20.

One of the first electrode 10 and the second electrode 20 is an anode and the other is a cathode. At least one of the first electrode 10 and the second electrode 20 may be a light-transmitting electrode, and the light-transmitting electrode may be made of, for example, a transparent conductor (e.g., indium tin oxide (ITO) or indium zinc oxide (IZO)), or a metal thin layer of a thin monolayer or multilayer. When one of the first electrode 10 and the second electrode 20 is a non-light-transmitting electrode, the one of the first electrode 10 and the second electrode 20 may be made of, for example, an opaque conductor (e.g., aluminum (Al)).

For example, the first electrode 10 and the second electrode 20 may be all light-transmitting electrodes.

The active layer 30 includes a p-type semiconductor and an n-type semiconductor to form a pn junction, and absorbs external light to generate excitons and then separates the generated excitons into holes and electrons.

On the other hand, a full width at half maximum (FWHM) may be used as an index showing wavelength selectivity selectively absorbing light in a given or predetermined wavelength region out of a visible ray region. The full width at half maximum (FWHM) is the width of a wavelength corresponding to a half of a maximum absorption point in a light absorption curve depending on a wavelength and may be defined based on absorbance measured by UV-Vis spectroscopy, when a specific definition is not otherwise provided. When the full width at half maximum (FWHM) is small, wavelength selectivity is increased by selectively absorbing light in a narrow wavelength region.

The active layer 30 may show a light absorption curve having a full width at half maximum (FWHM) of about 50 nm to about 150 nm. The active layer 30 may be a thin film formed by a deposition process or a solution process.

The active layer 30 may include a p-type semiconductor compound and a n-type semiconductor compound that are present uniformly. The compound for an organic photoelectric device may be a p-type semiconductor compound or a n-type semiconductor compound.

The active layer 30 may include a compound selected from the compound represented by Chemical Formula 1, the compound represented by Chemical Formula 2, and a combination thereof as a p-type semiconductor compound, and may further include a n-type semiconductor compound.

The n-type semiconductor compound may be subphthalocyanine or a subphthalocyanine derivative, fullerene or a fullerene derivative, thiophene or a thiophene derivative, or a combination thereof.

The active layer 30 may include a compound selected from the compound represented by Chemical Formula 1, the compound represented by Chemical Formula 2 and a combination thereof as a n-type semiconductor compound, and may further include a p-type semiconductor compound.

In addition, the active layer 30 may include the p-type semiconductor compound and the n-type semiconductor compound in a different volume ratio depending on their positions. When the first electrode is an anode, while the second electrode is a cathode, the active layer 30 may include the p-type semiconductor compound in a greater amount than the n-type semiconductor compound as closer to the anode, but the n-type semiconductor compound may be included in a greater amount than the p-type semiconductor compound as closer to the cathode. Herein, the p-type semiconductor compound and the n-type semiconductor compound may have a volume ratio changed gradually or in a stair way in a thickness direction.

The active layer 30 may be a single layer or a multilayer. The active layer 30 may be, for example, an intrinsic layer (I layer), a p-type layer/I layer, a I layer/n-type layer, a p-type layer/I layer/n-type layer, a p-type layer/n-type layer, etc.

The intrinsic layer (I layer) may include the compound of Chemical Formula 1 and the n-type semiconductor compound in a thickness (volume) ratio of about 1:100 to about 100:1. The compound of Chemical Formula 1 and the n-type semiconductor compound may be included in a thickness ratio ranging from about 1:50 to about 50:1 within the range, specifically, about 1:10 to about 10:1, and more specifically, about 1:1. Within the ranges, an exciton may be effectively produced and a pn junction may be effectively formed.

The p-type layer may include a p-type semiconductor compound, and the n-type layer may include an n-type semiconductor compound.

The active layer 30 may have a thickness of about 1 nm to about 500 nm, and specifically, about 5 nm to about 300 nm. When the active layer 30 has a thickness within the range, the active layer may effectively absorb light, effectively separate holes from electrons, and deliver them, thereby effectively improving photoelectric conversion efficiency.

In the organic photoelectric device 100, when light enters from the first electrode 10 and/or second electrode 20, and when the active layer 30 absorbs light having a given or predetermined wavelength region, excitons may be produced from the inside. The excitons are separated into holes and electrons in the active layer 30, and the separated holes are transported to an anode that is one of the first electrode 10 and second electrode 20 and the separated electrons are transported to the cathode that is the other of and the first electrode 10 and second electrode 20 so as to flow a current in the organic photoelectric device.

Hereinafter, an organic photoelectric device according to example embodiments is described with reference to FIG. 2.

Figure 2:
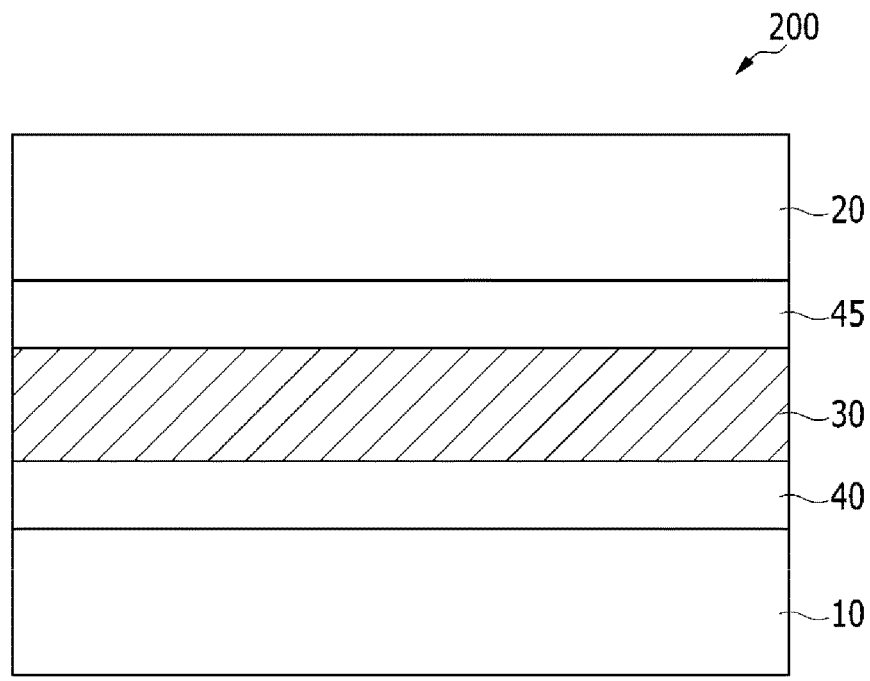
FIG. 2 is a cross-sectional view showing an organic photoelectric device according to example embodiments.

FIG. 2 is a cross-sectional view showing an organic photoelectric device according to example embodiments.

Referring to FIG. 2, an organic photoelectric device 200 according to the example embodiments includes a first electrode 10 and a second electrode 20 facing each other, and an active layer 30 between the first electrode 10 and the second electrode 20, like the example embodiment illustrated in FIG. 1.

However, the organic photoelectric device 200 according to example embodiments further includes charge auxiliary layers 40 and 45 between the first electrode 10 and the active layer 30, and the second electrode 20 and the active layer 30, unlike the example embodiment illustrated in FIG. 1. The charge auxiliary layers 40 and 45 may facilitate the transfer of holes and electrons separated from the active layer 30, so as to increase efficiency.

The charge auxiliary layers 40 and 45 may be at least one selected from a hole injection layer (HIL) for facilitating hole injection, a hole transport layer (HTL) for facilitating hole transport, an electron blocking layer (EBL) for reducing or preventing electron transport, an electron injection layer (EIL) for facilitating electron injection, an electron transport layer (ETL) for facilitating electron transport, and a hole blocking layer (HBL) for reducing or preventing hole transport.

The charge auxiliary layers 40 and 45 may include, for example, an organic material, an inorganic material, or an organic/inorganic material. The organic material may be an organic compound having hole or electron characteristics, and the inorganic material may be, for example, a metal oxide (e.g., molybdenum oxide, tungsten oxide, nickel oxide, etc).

The hole transport layer (HTL) may include one selected from, for example, poly(3,4-ethylenedioxythiophene):poly (styrenesulfonate) (PEDOT:PSS), polyarylamine-, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino]biphenyl ($\alpha$-NPD), m-MTDATA, 4,4',4"-tris(N-carbazolyl)-triphenylamine (TCTA), and a combination thereof, but is not limited thereto.

The electron blocking layer (EBL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino]biphenyl ($\alpha$-NPD), m-MTDATA, 4,4',4"-tris(N-carbazolyl)-triphenylamine (TCTA), and a combination thereof, but is not limited thereto.

The electron transport layer (ETL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

The hole blocking layer (HBL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

Either one of the charge auxiliary layers 40 and 45 may be omitted.

The organic photoelectric device may be applied to various fields, for example a solar cell, an image sensor, a photo-detector, a photo-sensor.

Hereinafter, an example of an image sensor including the organic photoelectric device is described referring to drawings. As an example of an image sensor, an organic CMOS image sensor is described.

Figure 3:
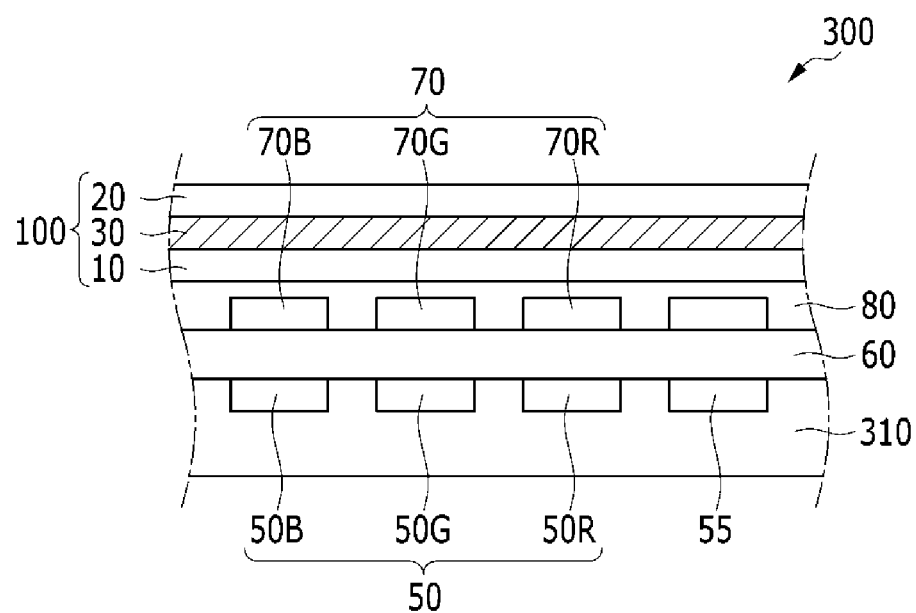
FIG. 3 is a schematic cross-sectional view showing an organic CMOS image sensor according to example embodiments.

FIG. 3 is a cross-sectional view of an organic CMOS image sensor according to example embodiments.

FIG. 3 exemplarily explains adjacent blue, green, and red pixels, but is not limited thereto. Hereinafter, a constituent element including "B" in the reference symbol refers to a constituent element included in the blue pixel, a constituent element including "G" refers to a constituent element included in the green pixel, and a constituent element including "R" in the reference symbol refers to a constituent element included in the red pixel.

Referring to FIG. 3, an organic CMOS image sensor 300 according to example embodiments includes a semiconductor substrate 310 integrated with a photo-sensing device 50 and a transmission transistor (not shown), a lower insulation layer 60, color filters 70B, 70G, and 70R, an upper insulation layer 80, and an organic photoelectric device 100.

The semiconductor substrate 310 may be a silicon substrate, and is integrated with the photo-sensing device 50 and the transmission transistor (not shown). The photo-sensing device 50 may be a photodiode. The photo-sensing device 50 and the transmission transistor may be integrated in each pixel, and as shown in the drawing, the photo-sensing device 50 includes a blue pixel photo-sensing device 50B, a green pixel photo-sensing device 50G, and a red pixel photo-sensing device 50R. The photo-sensing device 50 senses light, and the information sensed by the photo-sensing device 50 is transferred by the transmission transistor.

Metal wires (not shown) and pads (not shown) are formed on the semiconductor substrate 310. In order to decrease signal delay, the metal wires and pads may be made of a metal having low resistivity, for example, aluminum (Al), copper (Cu), silver (Ag), and alloys thereof, but is not limited thereto.

The lower insulation layer 60 is formed on the metal wires and pads. The lower insulation layer 60 may be made of an inorganic insulating material (e.g., silicon oxide and/or silicon nitride), or a low dielectric constant (low K) material (e.g., SiC, SiCOH, SiCO, and SiOF). The lower insulation layer 60 has a trench (not shown) exposing each photo-sensing device 50B, 50G, and 50R of each pixel. The trench may be filled with fillers.

A color filter layer 70 is formed on the lower insulation layer 60. The color filter layer 70 includes the blue filter 70B formed in the blue pixel, the green filter 70G formed in the green pixel and the red filter 70R formed in the red pixel.

The upper insulation layer 80 is formed on the color filter layer 70. The upper insulation layer 80 eliminates a step caused by the color filters 70 and smoothes the surface. The upper insulation layer 80 and lower insulation layer 60 may include a contact hole (not shown) exposing a pad.

The organic photoelectric device 100 is formed on the upper insulation layer 80. The organic photoelectric device 100 includes a first electrode 10, an active layer 30, and a second electrode 20 as described above.

The first electrode 10 and the second electrode 20 may be transparent electrodes, and the active layer 30 is the same as described above. The active layer 30 selectively absorbs light in one wavelength region of green, blue and red wavelength regions, and replaces one color filter of green, blue and red pixels.

When light enters from the second electrode 20, the light in a particular wavelength region may be mainly absorbed in the active layer 30 and photoelectrically converted, while the light in the rest of the wavelength regions passes through first electrode 10 and may be sensed in the photo-sensing devices 50B, 50G, and 50R.

In FIG. 3, the organic photoelectric device 100 of FIG. 1 is included, but it is not limited thereto, and thus the organic photoelectric device 200 of FIG. 2 may be applied in the same manner.

Figure 4:
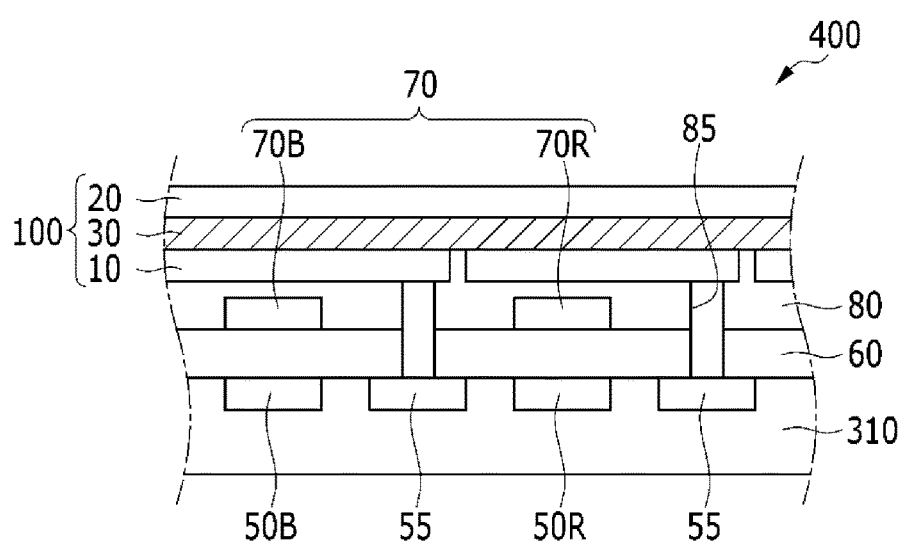
FIG. 4 is a schematic cross-sectional view showing an organic CMOS image sensor according to example embodiments.

Referring to FIG. 4, an organic CMOS image sensor 400 according to example embodiments includes a semiconductor substrate 310 integrated with photo-sensing devices 50B and 50R, a transmission transistor (not shown), a charge storage device 55, a lower insulation layer 60, a color filter layer 70, an upper insulation layer 80, and an organic photoelectric device 100.

The semiconductor substrate 310 may be a silicon substrate, and is integrated with the photo-sensing device 50, the transmission transistor (not shown), and the charge storage device 55. The photo-sensing devices 50R and 50B may be photodiodes.

The photo-sensing devices 50B and 50R, the transmission transistor, and/or the charge storage device 55 may be integrated in each pixel, and as shown in the drawing, the photo-sensing devices 50B and 50R may be respectively included in a blue pixel and a red pixel and the charge storage device 55 may be included in a green pixel.

The photo-sensing devices 50B and 50R sense light, the information sensed by the photo-sensing devices may be transferred by the transmission transistor, the charge storage device 55 is electrically connected with the organic photo-electric device 100, and the information of the charge storage device 55 may be transferred by the transmission transistor.

In the drawings, the photo-sensing devices 50B and 50R are, for example, arranged in parallel without limitation, and the blue photo-sensing device 50B and the red photo-sensing device 50R may be stacked in a vertical direction.

A metal wire (not shown) and a pad (not shown) are formed on the semiconductor substrate 310. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be positioned under the photo-sensing devices 50B and 50R.

The lower insulation layer 60 is formed on the metal wire and the pad. The lower insulation layer 60 may be made of an inorganic insulating material (e.g., a silicon oxide and/or a silicon nitride), or a low dielectric constant (low K) material (e.g., SiC, SiCOH, SiCO, and SiOF). The lower insulation layer 60 has a trench exposing the charge storage device 55. The trench may be filled with fillers.

A color filter layer 70 is formed on the lower insulation layer 60. The color filter layer 70 includes a blue filter 70B formed in the blue pixel and selectively transmitting blue light and a red filter 70R formed in the red pixel and selectively transmitting red light. In example embodiments, a green filter is not included, but a green filter may be further included.

The color filter layer 70 may be omitted. For example, when the blue photo-sensing device 50B and the red photo-sensing device 50R are stacked in a vertical direction, the blue photo-sensing device 50B and the red photo-sensing device 50R may selectively absorb light in each wavelength region depending on their stack depth, and the color filter layer 70 may not be equipped.

The upper insulation layer 80 is formed on the color filter layer 70. The upper insulation layer 80 eliminates a step caused by the color filter layer 70 and smoothes the surface. The upper insulation layer 80 and the lower insulation layer 60 may include a contact hole (not shown) exposing a pad, and a through-hole 85 exposing the charge storage device 55 of the green pixel.

The organic photoelectric device 100 is formed on the upper insulation layer 80.

When light enters from the second electrode 20, the light in a green wavelength region may be mainly absorbed in the active layer 30 and photoelectrically converted, while the light in the rest of the wavelength regions passes through first electrode 10 and may be sensed in the photo-sensing devices 50B and 50R.

An organic photoelectric device including the active layer 30 may include a compound selectively absorbing light in a particular wavelength region. Herein, the organic photoelectric device may be usefully applied to an image sensor having a stacking structure shown in FIG. 4. The organic photoelectric device has a stacking structure selectively absorbing light in a particular wavelength region and thus may reduce the size of the image sensor and realized a down-sized image sensor.

In FIG. 4, the organic photoelectric device 100 of FIG. 1 is included, but it is not limited thereto, and thus the organic photoelectric device 200 of FIG. 2 may be applied in the same manner.

Figure 5:
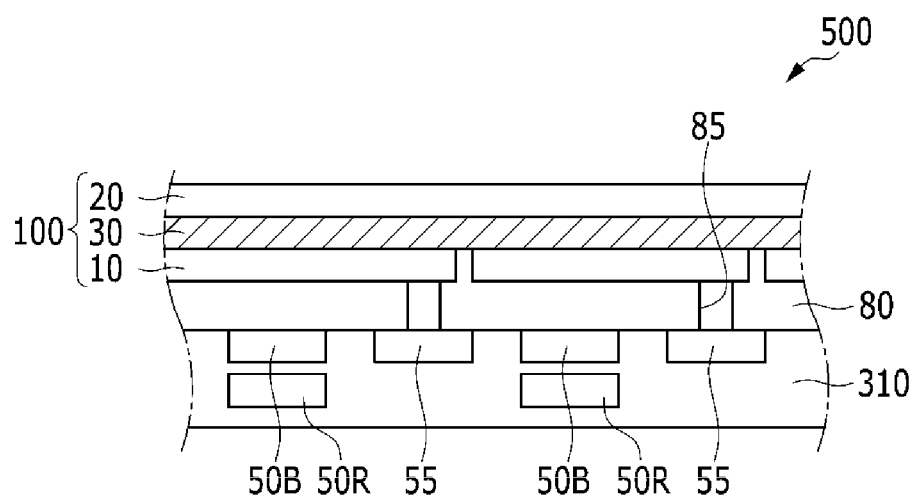
FIG. 5 is a schematic cross-sectional view showing an organic CMOS image sensor according to example embodiments.

FIG. 5 is a schematic cross-sectional view of an organic CMOS image sensor according to example embodiments.

Referring to FIG. 5, the organic CMOS image sensor 500 according to example embodiments includes a green photoelectric device (G) selectively absorbing light in a green wavelength region, a blue photoelectric device (B) selectively absorbing light in a blue wavelength region, and a red photoelectric device selectively absorbing light in a red wavelength region that are stacked.

The organic CMOS image sensor 500 according to example embodiments includes a semiconductor substrate 310 integrated with photo-sensing devices 50B and 50R, a transmission transistor (not shown), a charge storage device 55, an insulation layer 80, and an organic photoelectric device 100, like the example embodiment illustrated in FIG. 5.

Figure 6:
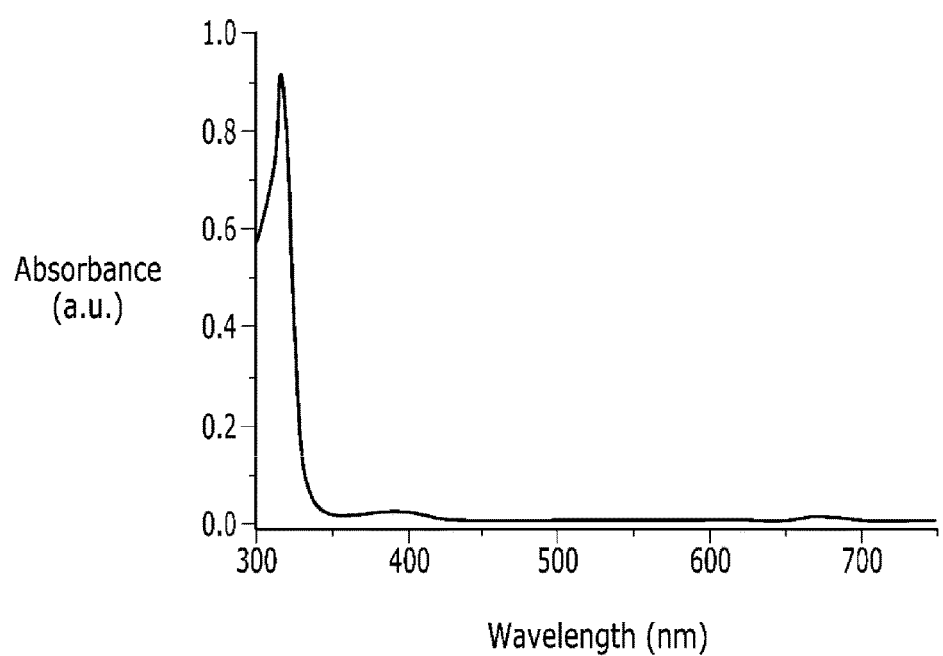
FIG. 6 is a graph showing light absorption characteristics showing the compound represented by Chemical Formula 1a according to Synthesis Example 1.

However, the organic CMOS image sensor 500 according to the example embodiment illustrated in FIG. 6 includes the blue photo-sensing device 50B and the red photo-sensing device 50R that are stacked and does not include a color filter layer 70, unlike the example embodiment illustrated in FIG. 5. The blue photo-sensing device 50B and the red photo-sensing device 50R are electrically connected with the charge storage device 55, and the information of the charge storage device 55 may be transferred by the transmission transistor (not shown). The blue photo-sensing device 50B and the red photo-sensing device 50R may selectively absorb light in each wavelength region depending on a stack depth.

The organic photoelectric device including the compound for an organic photoelectric device shows improved selective absorption in a particular region and may be usefully applied to the stacking structure of an image sensor shown in FIG. 5. This stacking structure may further reduce the size of the image sensor and realize a down-sized image sensor.

In the drawing, the red photoelectric device, the green photoelectric device, and the blue photoelectric device are sequentially stacked, but the stack order may be changed without limitation.

In FIG. 5, the organic photoelectric device 100 of FIG. 1 is included, but it is not limited thereto, and thus the organic photoelectric device 200 of FIG. 2 may be applied in the same manner.

The image sensor may be applied to various electronic devices, for example, a mobile phone and/or a digital camera, but is not limited thereto.

Hereinafter, the present disclosure is illustrated in more detail with reference to examples. However, these are examples, and the present disclosure is not limited thereto.

SYNTHESIS EXAMPLES

Synthesis Example 1

A compound represented by Chemical Formula 1a is synthesized according to Reaction Scheme 1.

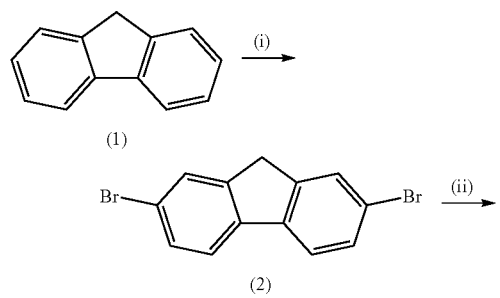

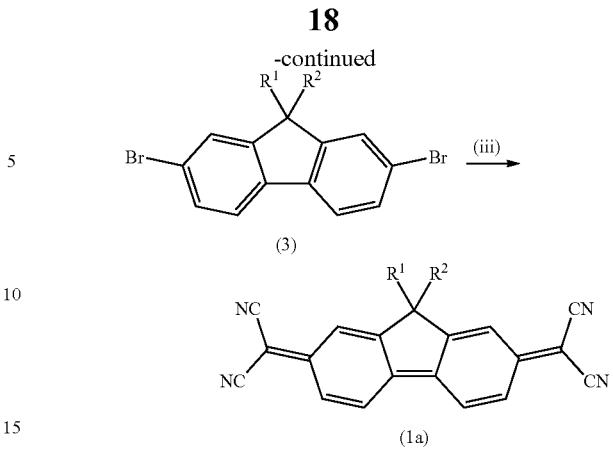

In Reaction Scheme 1, $R^1$ and $R^2$ are octyl groups.

(i) Synthesis of 2,7-dibromo-9H-fluorene (Compound (2))

Fluorene (Compound (1)) is dissolved in chloroform in a round flask and decreased down to 0° C. Then, bromine is slowly added thereto in a dropwise fashion, the mixture is stirred at room temperature 24° C. for 20 hours, and a sodium hydrogen sulfite ($NaHSO_3$) aqueous solution is added thereto, completing a reaction. Subsequently, a product therefrom is extracted by using chloroform, and an organic solution layer therefrom is several times cleaned and recrystallized by using chloroform and ethanol, obtaining a Compound (2).

(ii) Synthesis of 2,7-dibromo-9,9-dioctyl-9H-fluorene (Compound (3))

2,7-dibromo-9H-fluorene and KOH is stirred with dimethyl sulfoxide under an inert gas (argon, Ar) for 1 hour, 1-bromoctane is slowly added thereto, and the mixture is refluxed at 90° C. for one day. Then, water is used to stop the reaction, diethylether is used to perform an extraction, and hexane in a mobile phase is used to purify an extract therefrom through column chromatography. Finally, ethanol (100 mL) and chloroform (10 mL) are used to perform recrystallization, obtaining the Compound (3).

(iii) Synthesis of Compound Represented by Chemical Formula 1a

Malononitrile (0.58 g) and sodium hydride (NaH) (1.2 g) dispersed in mineral oil with purity of 60% are added to tetrahydrofuran (THF) under an inert gas (argon, Ar) at −5° C., and the mixture is stirred. Then, a tetrakis(triphenylphosphine)-palladium catalyst and 2,7-dibromo-9,9-dioctyl-9H-fluorene (Compound (3)) are added thereto after removing a constant-temperature water bath 30 minutes later, and the mixture is reacted at 100° C. After 4 hours, a hydrochloric acid aqueous solution in a concentration of 6 mol is added thereto in a dropwise fashion at −5° C. Then, after another 4 hours, a saturated bromine aqueous solution is added thereto in a dropwise fashion at 0° C., and the mixture is reacted at room temperature (24° C.) for greater than or equal to 8 hours.

Then, dichloromethane (DCM) is used to perform an extraction, and an extract therefrom is purified with hexane and dichloromethane in a volume ratio of 2:1 as a developing solvent to purify through column chromatography, obtaining a compound represented by Chemical Formula 1a.

The compound represented by Chemical Formula 1a shows $^1$H NMR result.

$^1$H NMR (CDCl$_3$, 400 MHz) δ: 7.71 (d, J=8 Hz, 1H), 7.66 (d, J=1.6 Hz, 1H), 7.60 (d, J=8.4 Hz, 1H), 7.52 (m, 2H), 7.44 (d, J=8.4 Hz, 1H), 2.09-1.92 (m, 4H), 1.37-0.97 (m, 24H), 0.92-0.76 (m, 6H), 0.67-0.49 (m, 4H)

Synthesis Example 2

A compound represented by Chemical Formula 1b is synthesized according to Reaction Scheme 2.

[Reaction Scheme 2]

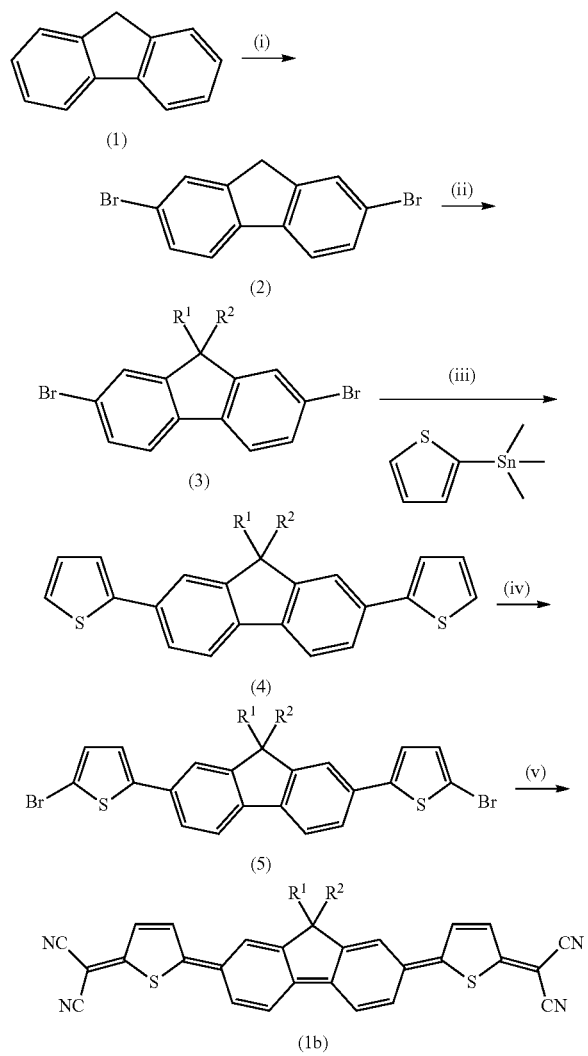

In Reaction Scheme 2, R$^1$ and R$^2$ are octyl groups.

(i) Synthesis of 2,7-dibromo-9H-fluorene (Compound (2)) and (ii) Synthesis of 2,7-dibromo-9,9-dioctyl-9H-fluorene (Compound (3))

Then, 2,7-dibromo-9,9-dioctyl-9H-fluorene (Compound (3)) is synthesized according to the same synthesis method as the processes (i) and (ii) of Synthesis Example 1.

(iii) Synthesis of Compound (4)

2 g of toluene is stirred under an inert gas (argon, Ar) at −5° C. Then, 2,7-dibromo-9,9-dioctyl-9H-fluorene (Compound (3)) and trimethyl(thiophen-2-yl)stannane are put in a reactor, and tetrakistriphenylphosphine-palladium as a catalyst is put in the reactor, and the temperature of the reactor is increased up to 90° C. to react the mixture for 4 hours.

Then, dichloromethane (DCM) is used to perform an extraction, and an extract therefrom is purified with hexane and dichloromethane in a volume ratio of 2:1 as a developing solvent through column chromatography, obtaining a Compound (4).

(iv) Synthesis of Compound (5)

The Compound (4) is brominated to obtain a Compound (5).

(v) Synthesis of Compound Represented by Chemical Formula 1b

Malononitrile (0.58 g) and sodium hydride (NaH) (1.2 g) dispersed in mineral with purity of 60% under an inert gas (argon, Ar) at −5° C. are added to tetrahydrofuran (THF), and the mixture is stirred.

After 30 minutes, a constant temperature water bath is removed, a tetrakistriphenylphosphine-palladium catalyst and Compound (5) are added thereto, and the mixture is reacted at 100° C. Four hours later, a hydrochloric acid aqueous solution in a concentration of 6 moles is added thereto in a dropwise fashion at −5° C., and the mixture is stirred again. After another 4 hours, a saturated bromine aqueous solution is added thereto again in a dropwise fashion at 0° C., and the obtained mixture is reacted at room temperature (24° C.) for greater than or equal to 8 hours.

Then, dichloromethane (DCM) is used to perform an extraction, and an extract therefrom is purified with hexane and dichloromethane in a volume ratio of 2:1 as a developing solvent through column chromatography, obtaining a compound represented by Chemical Formula 1 b.

Synthesis Example 3

A compound represented by Chemical Formula 1c is synthesized according to Reaction Scheme 3.

[Reaction Scheme 3]

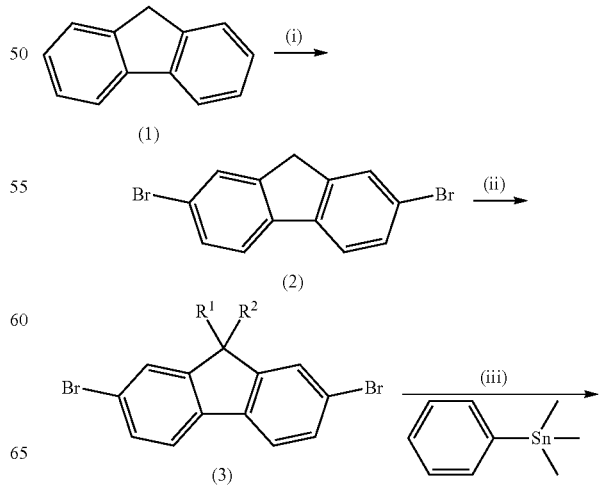

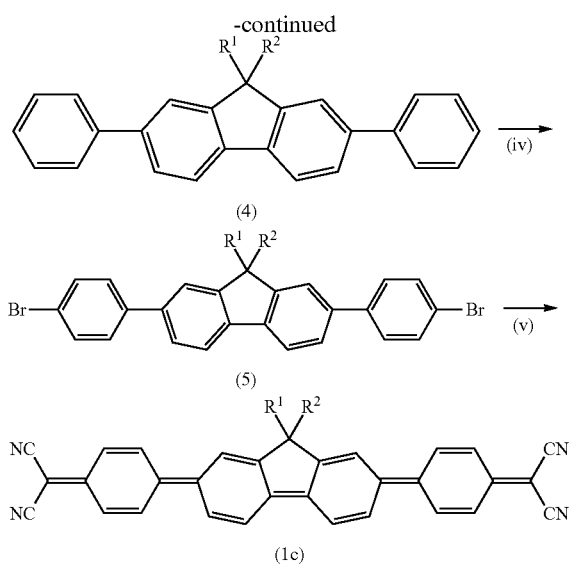

In Reaction Scheme 3, $R^1$ and $R^2$ are octyl groups.

(i) Synthesis of 2,7-dibromo-9H-fluorene (Compound (2)) and (ii) Synthesis of 2,7-dibromo-9,9-dioctyl-9H-fluorene (Compound (3))

2,7-dibromo-9,9-dioctyl-9H-fluorene (Compound (3)) is synthesized according to the same method as the processes (i) and (ii) according to Synthesis Example 1.

(iii) Synthesis of Compound (4)

2 g of toluene is stirred under an inert gas (argon, Ar) at −5° C. 2,7-dibromo-9,9-dioctyl-9H-fluorene (Compound (3)) and trimethyl(phenyl)stannane) are put in a reactor, tetrakistriphenylphosphine-palladium as a catalyst is added thereto, and then, the temperature of the reactor is increased up to 90° C., and the mixture is reacted for 4 hours.

Then, dichloromethane (DCM) is used to perform an extraction, and an extract therefrom is purified with hexane and dichloromethane in a volume ratio of 2:1 as a developing solvent through column chromatography, obtaining the Compound (4).

(iv) Synthesis of Compound (5)

The Compound (4) is brominated to obtain a Compound (5).

(v) Synthesis of Compound Represented by Chemical Formula 1c

Malononitrile (0.58 g) and sodium hydride (NaH) (1.2 g) dispersed in mineral oil with purity of 60% under an inert gas (argon, Ar) at −5° C. are added to tetrahydrofuran (THF), and the mixture is stirred. After 30 minutes, a constant temperature water bath is removed, a (tetrakis(triphenylphosphine)-palladium catalyst and Compound (5) are added thereto, and the mixture is reacted at 100° C. After 4 hours, a hydrochloric acid aqueous solution in a concentration of 6 moles at −5° C. is added thereto in a dropwise fashion, and the mixture is stirred again. Another 4 hours later, a saturated bromine aqueous solution is added thereto again in a dropwise fashion at 0° C., and the obtained mixture is reacted at room temperature (24° C.) for greater than or equal to 8 hours.

Then, dichloromethane (DCM) is used to perform an extraction, and an extract therefrom is purified with hexane and dichloromethane in a volume ratio of 2:1 as a developing solvent through column chromatography, obtaining a compound represented by Chemical Formula 1c.

Comparative Synthesis Example 1

A compound represented by Chemical Formula 1d is synthesized according to Reaction Scheme 4.

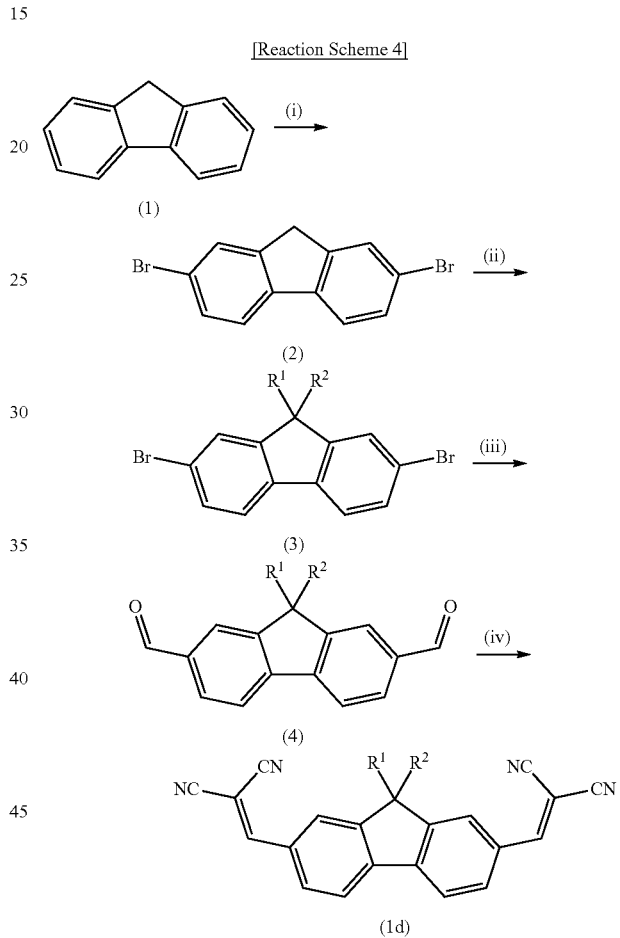

In Reaction Scheme 4, $R^1$ and $R^2$ are octyl groups.

(i) Synthesis of 2,7-dibromo-9H-fluorene (Compound (2)), and (ii) Synthesis of 2,7-dibromo-9,9-dioctyl-9H-fluorene (Compound (3))

2,7-dibromo-9,9-dioctyl-9H-fluorene (Compound (3)) is synthesized according to the same method as the processes (i) and (ii) of Synthesis Example 1.

(iii) Synthesis of 9,9-dioctyl-9H-fluorene-2,7-dicarbaldehyde (Compound (4))

The 2,7-dibromo-9,9-dioctyl-9H-fluorene (Compound (3)) is dissolved in anhydrous tetrahydrofuran, n-butyl lithium (n-BuLi) is slowly added thereto, and the mixture is stirred at −78° C. for 1 hour. After 1 hour, anhydrous dimethyl formamide (DMF) is added thereto, and the mixture is reacted. The reaction is stopped by using water, and dichloromethane (DCM) is used to perform an extraction. Then, an extract therefrom is purified with 10 vol % of ethylacetate (EA) and a hexane solution through column chromatography.

(iv) Synthesis of Compound Represented by Chemical Formula 1d 9,9-dioctyl-9H-fluorene-2,7-dicarbaldehyde and malononitrile are dissolved in glacial acetic acid, piperidine is slowly added thereto, and the mixture is reacted. The reaction is stopped by using a thin hydrochloric acid solution, dichloromethane (DCM) is used to perform an extraction, and an extract therefrom is purified with a 20 volume % of ethylacetate (EA) and a hexane solution through column chromatography, obtaining a compound represented by Chemical Formula 1d.

The compound represented by Chemical Formula 1d has the following $^1$H NMR result.

$^1$H NMR (CDCl$_3$, 400 MHz) δ: 7.95 (m, 6H), 7.86 (s, 2H), 2.07-2.01 (m, 4H), 1.34-0.96 (m, 23H), 0.89-0.73 (m, 6H), 0.63-0.52 (m, 4H)

Comparative Synthesis Example 2

A compound represented by Chemical Formula 1e is synthesized according to Reaction Scheme 5.

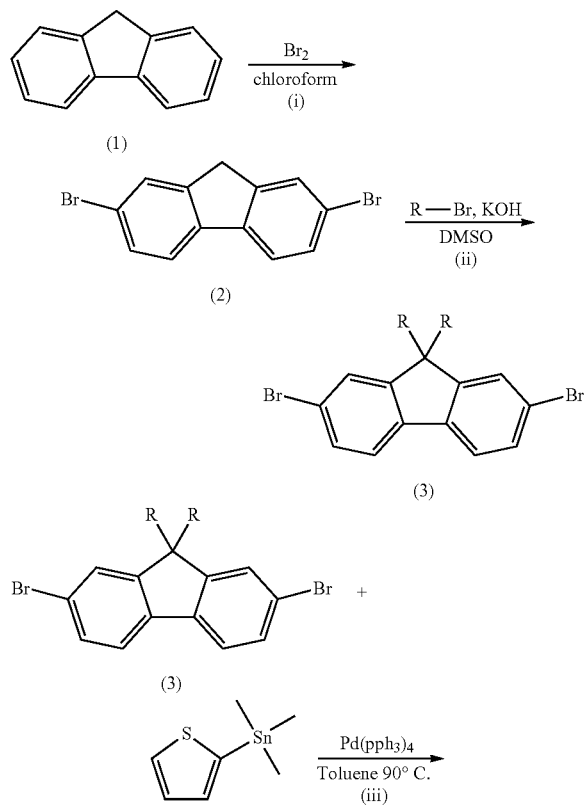

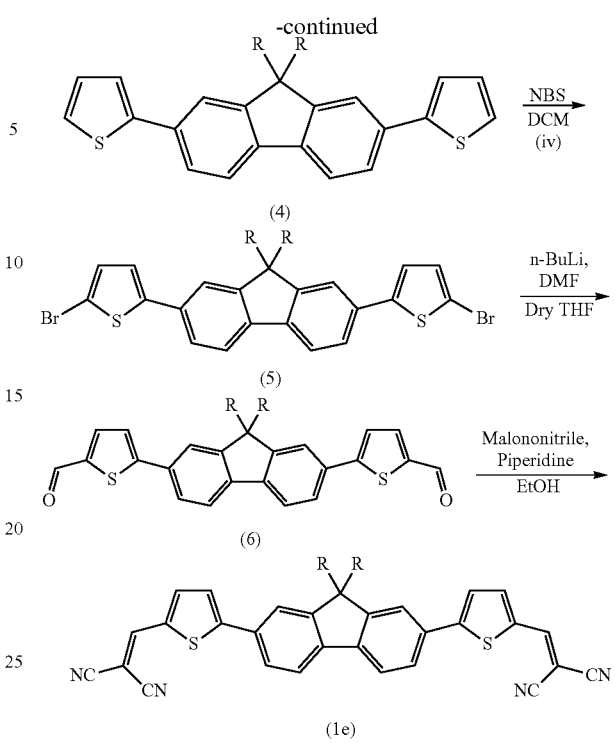

In Reaction Scheme 5, R is an octyl group.

(i) Synthesis of 2,7-dibromo-9H-fluorene (Compound (2)) and (ii) Synthesis of 2,7-dibromo-9,9-dioctyl-9H-fluorene (Compound (3))

2,7-dibromo-9,9-dioctyl-9H-fluorene (Compound (3)) is synthesized according to the same method as the processes (i) and (ii) of Synthesis Example 1.

(iii) Synthesis of Compound (4)

2 g of toluene is put in a reactor under an inert gas (argon, Ar) at −5° C. and stirred. Then, 2,7-dibromo-9,9-dioctyl-9H-fluorene (Compound (3)) and trimethyl(thiophen-2-yl)stannane are put in the reactor, tetrakis(triphenylphosphine)-palladium as a catalyst is added thereto, and the mixture is reacted for 4 hours by increasing its temperature up to 90° C.

Subsequently, dichloromethane (DCM) is used to perform an extraction, and an extract therefrom is purified with hexane and dichloromethane in a volume ratio of 2:1 as a developing solvent through column chromatography, obtaining 2,7-di(2-thienyl)-9,9-dioctylfluorene (Compound 4).

(iv) Syntheses of Compounds (5) and (6)

The Compound (4) is brominated to obtain a Compound (5), the Compound (5) is dissolved in anhydrous tetrahydrofuran, n-butyl lithium (n-BuLi) is slowly added thereto at −78° C., and the mixture is stirred for 1 hour. After 1 hour, anhydrous dimethylformamide (DMF) is added thereto, and the mixture is reacted. The reaction is stopped by using water, and dichloromethane (DCM) is used to perform an extraction. Then, an extract therefrom is purified with 10 volume % of ethylacetate (EA) and a hexane solution through column chromatography, obtaining a compound 6.

(v) Synthesis of Compound Represented by
Chemical Formula 1e 5,5'-(9H-fluorene-2,7-diyl)bis(thiophene-2-carbaldehyde) is put in a reactor under an inert gas (argon, Ar) at room temperature, ethanol, malononitrile, and piperidine are added thereto, and the mixture is stirred and reacted for 2 hours.

Then, dichloromethane (DCM) is used to perform an extraction, and an extract therefrom is purified with hexane and dichloromethane in a volume ratio of 2:1 as a developing solvent through column chromatography, obtaining a compound represented by Chemical Formula 1c.

Comparative Synthesis Example 3

A compound represented by Chemical Formula 1f is synthesized according to Reaction Scheme 6.

[Reaction Scheme 6]

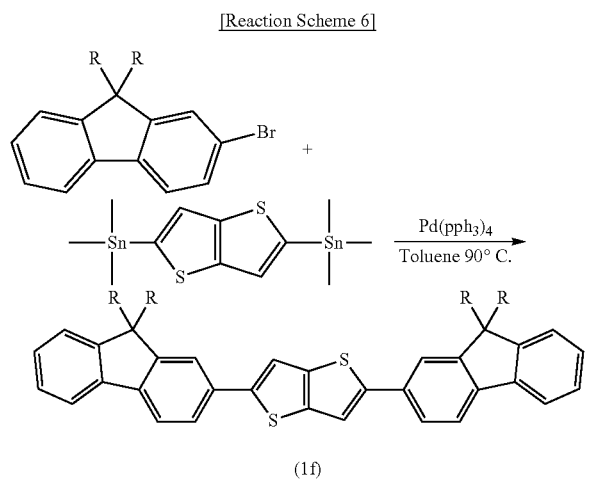

(1f)

In Reaction Scheme 6, R is an octyl group.

10 g of toluene is put in a reactor and stirred under inert gas (argon, Ar) at −5° C. 2-bromo-9H-fluorene (2 eq., 0.24 g) and 2,5-bis(trimethylstannyl)thieno[3,2-b]thiophenetrimethyl(thiophen-2-yl)stannane (1 eq., 0.45 g) are put in the reactor, tetrakis(triphenylphosphine)-palladium as a catalyst is added thereto, and the mixture reacted for 4 hours at 90° C. by increasing its temperature up to 90° C.

Then, dichloromethane (DCM) is used to perform an extraction, and an extract therefrom is purified with hexane and dichloromethane in a volume ratio of 2:1 as a developing solvent through column chromatography, obtaining a compound represented by Chemical Formula 1f.

Light Absorption Characteristics

Light absorption characteristics of each solution obtained by dissolving 0.44 mg of the compound represented by Chemical Formula 1a according to Synthesis Example 1 in 50 mL of chloroform and 1.37 mg of the compound represented by Chemical Formula 1d according to Comparative Synthesis Example 1 in 96 mL of chloroform are evaluated by radiating an ultraviolet (UV)-visible ray (UV-Vis) with Cary 5000 UV spectroscopy (Varian Medical System)

Figure 7:
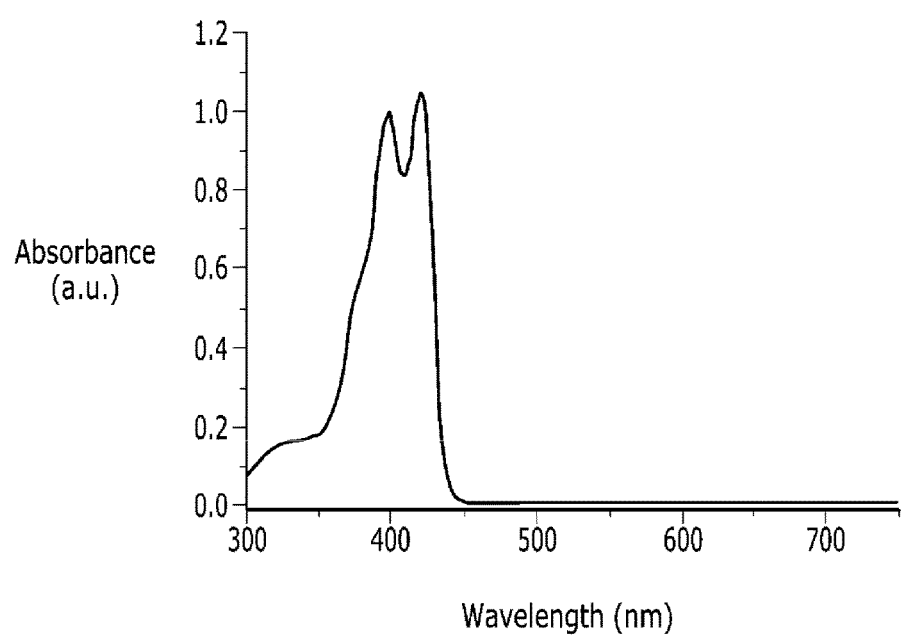
FIG. 7 is a graph showing light absorption characteristics of the compound represented by Chemical Formula 1d according to Comparative Synthesis Example 1.

The results are respectively shown in FIGS. 6 and 7. Referring to FIG. 6, the compound represented by Chemical Formula 1a according to Synthesis Example 1 shows narrow and strong absorption characteristics at 318 nm, referring to FIG. 7, the compound represented by Chemical Formula 1d according to Comparative Synthesis Example 1 shows two absorption peaks separated at 398 nm and 421 nm, which is broader than that of the compound shown in FIG. 6

In addition, in the graphs of FIGS. 6 and 7, the compound represented by Chemical Formula 1a according to Synthesis Example 1 and the compound represented by Chemical Formula 1d according to Comparative Synthesis Example 1 respectively have energy bandgaps of 3.68 eV and 2.80 eV through extrapolation of a light absorption-starting point. The results are provided in Table 1.

Electric Characteristics

The compound represented by Chemical Formula 1a according to synthesis Example 1 and the compound represented by Chemical Formula 1d according to Comparative Synthesis Example 1 are measured regarding LUMO and HOMO energy levels through cyclic voltammetry (CV). Herein, a glassy carbon electrode as a work electrode, a platinum electrode as a counter electrode, and a silver/silver ion (Ag/Ag$^+$) electrode in a methyl cyanide aqueous solution including 0.1 M n-butyltetraammonium hexafluorophosphonate (n-Bu$_4$NPF$_6$) and 0.01 M silver nitrate as a reference electrode, and a solution obtained by dissolving butyltetraammonium hexafluorophosphonate in a concentration of 0.01 M in chloroform are prepared. Then, an experiment is performed under a voltage transformation condition of 0.1 V/s by using ferrocene as a reference material to reduce an experimental error. The results from the experiment are provided in Table 1.

TABLE 1

| | Ultraviolet (UV) spectroscopy | | Cyclic voltammetry method | | |
|---|---|---|---|---|---|
| | $\lambda_{max}$ (nm) | $E_g$ (eV) | HOMO (eV) | LUMO (eV) | Energy bandgap (eV) |
| Synthesis Example 1 Chemical Formula 1a | 318 | 3.68 | −7.16 | −3.50 | 3.66 |
| Comparative Synthesis Example 1 Chemical Formula 1d | 398, 421 | 2.80 | −6.42 | −3.62 | 2.8 |

Referring to Table 1, the compound represented by Chemical Formula 1a according to Synthesis Example 1 shows relatively high HOMO and a relatively large bandgap and thus improved absorption wavelength selectivity. On the contrary, the compound represented by Chemical Formula 1d according to Comparative Synthesis Example 1 shows a relatively small bandgap and thus a relatively broad and wide absorption wavelength.

While this disclosure has been described in connection with what is presently considered to be practical example embodiments, it is to be understood that the inventive concepts are not limited to the disclosed embodiments, but, on the contrary, is intended to cover various modifications and equivalent arrangements included within the spirit and scope of the appended claims.

What is claimed is:

1. A compound for an organic photoelectric device comprising at least one of a compound represented by Chemical Formula 1 and a compound represented by Chemical Formula 2:

[Chemical Formula 1]

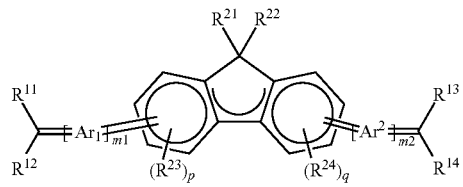

[Chemical Formula 2]

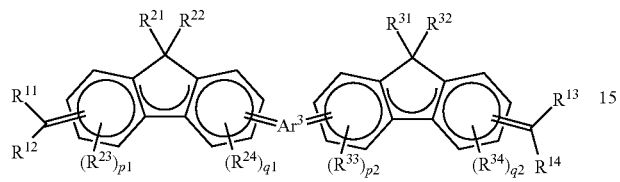

wherein, in Chemical Formulae 1 and 2,
each of $R^{11}$ to $R^{14}$ are independently one of a chloro group (—Cl), a bromo group (—Br), a substituted or unsubstituted $C_1$ to $C_{10}$ alkyl group, a cyano group (—CN), and a combination thereof,
each of $R^{21}$, $R^{22}$, $R^{31}$, and $R^{32}$ are independently one of hydrogen, a chloro group (—Cl), a bromo group (—Br), a substituted or unsubstituted $C_1$ to $C_{30}$ alkyl group, and a combination thereof or are optionally linked to provide a Spiro structure with a fluorene ring,
each of $R^{23}$, $R^{24}$, $R^{33}$, and $R^{34}$ are independently one of hydrogen, a chloro group (—Cl), a bromo group (—Br), a substituted or unsubstituted $C_1$ to $C_{10}$ alkyl group, a cyano group (—CN), and a combination thereof,
each of $Ar^1$, and $Ar^2$ are independently one of a substituted or unsubstituted $C_6$ to $C_{30}$ arylene group, a substituted or unsubstituted $C_3$ to $C_{30}$ heteroarylene group that does not include a substituted or unsubstituted thiophene group, and a combination thereof,
$Ar^3$ is one of a substituted or unsubstituted $C_6$ to $C_{30}$ arylene group, a substituted or unsubstituted $C_3$ to $C_{30}$ heteroarylene group, and a combination thereof,
each of p, p1, p2, q, q1, and q2 are independently an integer ranging from 0 to 3, and
each of m1 and m2 are 1.

2. The compound of claim 1, wherein in Chemical Formula 1 or 2, at least one of $R^{11}$ to $R^{14}$ is a cyano group (—CN).

3. The compound of claim 1, wherein in Chemical Formula 1 or 2, each of $R^{21}$, $R^{22}$, $R^{31}$, and $R^{32}$ are independently one of a $C_1$ to $C_{30}$ alkyl group substituted with an aryl group and a $C_1$ to $C_{30}$ alkyl group substituted with a cycloalkyl group.

4. The compound of claim 1, wherein in Chemical Formula 1 or 2, each of $R^{21}$, $R^{22}$, $R^{31}$, and $R^{32}$ are independently a $C_1$ to $C_{30}$ alkyl group where a methylene group (—(CH$_2$)—) that is not adjacent to a fluorene group is replaced by one of an arylene group and a cycloalkylene group.

5. The compound of claim 1, wherein in Chemical Formula 1 or 2, at least two to four of $R^{11}$ to $R^{14}$ are a cyano group (—CN).

6. The compound of claim 1, wherein in Chemical Formulae 1 and 2, each of $Ar^1$, and $Ar^2$ is one of a substituted or unsubstituted phenylene group, a substituted or unsubstituted thienothiophene group, and a combination thereof, and $Ar^3$ is one of a substituted or unsubstituted phenylene group, a substituted or unsubstituted thiophene group, a substituted or unsubstituted thienothiophene group, and a combination thereof.

7. The compound of claim 1, wherein the compound represented by Chemical Formula 1 is a compound represented by one of Chemical Formulae 1-1 to 1-3:

[Chemical Formula 1-1]

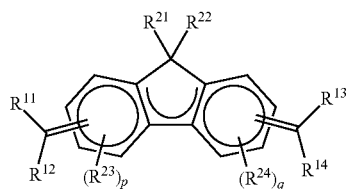

[Chemical Formula 1-2]

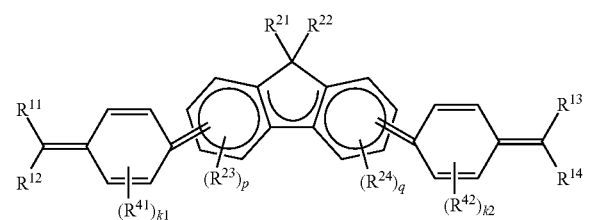

[Chemical Formula 1-3]

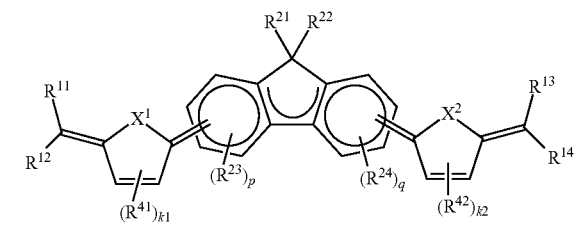

wherein, in Chemical Formulae 1-1 to 1-3,
each of $R^{11}$ to $R^{14}$ are independently one of a chloro group (—Cl), a bromo group (—Br), a substituted or unsubstituted $C_1$ to $C_{10}$ alkyl group, a cyano group (—CN), and a combination thereof,
each of $R^{21}$ and $R^{22}$ are independently one of hydrogen, a chloro group (—Cl), a bromo group (—Br), a substituted or unsubstituted $C_1$ to $C_{30}$ alkyl group, and a combination thereof or are optionally linked to provide a Spiro structure with a fluorene ring,
each of $R^{23}$, $R^{24}$, $R^{41}$, and $R^{42}$ are independently one of hydrogen, a chloro group (—Cl), a bromo group (—Br), a substituted or unsubstituted $C_1$ to $C_{10}$ alkyl group, a cyano group (—CN), and a combination thereof,
each of p and q are integers ranging from 0 to 3,
each of k1 and k2 correspond to the number of hydrogen in each aromatic ring, and
each of $X^1$ and $X^2$ are independently 0.

8. The compound of claim 7, wherein in Chemical Formulae 1-1 to 1-3, at least one of $R^{11}$ to $R^{14}$ is a cyano group (—CN).

9. The compound of claim 7, wherein in Chemical Formulae 1-1 to 1-3, at least two to four of $R^{11}$ to $R^{14}$ are a cyano group (—CN).

10. The compound of claim 1, wherein the compound has a maximum absorption peak ($\lambda_{max}$) in a wavelength region in a thin film state of about 300 nm to about 720 nm.

11. The compound of claim 1, wherein the compound shows a light absorption curve having a full width at half maximum (FWHM) in a thin film state of about 50 nm to about 150 nm.

12. The compound of claim 1, wherein the compound is one of a p-type semiconductor compound and an n-type semiconductor compound.

13. The compound of claim 1, wherein the compound has a bandgap of about 2.0 eV to about 4.0 eV.

14. The compound of claim 1, wherein the compound has a LUMO level of about 2.0 eV to about 4.2 eV.

15. An organic photoelectric device comprising:
a first electrode and a second electrode facing each other, and
an active layer between the first electrode and the second electrode, the active layer including the compound of claim 1.

16. The organic photoelectric device of claim 15, wherein in Chemical Formula 1 or 2, at least one of $R^{11}$ to $R^{14}$ is a cyano group (—CN).

17. The organic photoelectric device of claim 15, wherein in Chemical Formula 1 or 2, at least two to four of $R^{11}$ to $R^{14}$ are a cyano group (—CN).

18. An image sensor comprising the organic photoelectric device of claim 15.

19. The image sensor of claim 18, further comprising:
a semiconductor substrate integrated with a plurality of first photo-sensing devices configured to sense light in a blue wavelength region and a plurality of second photo-sensing devices configured to sense light in a red wavelength region,
wherein the organic photoelectric device is on the semiconductor substrate and is configured to selectively absorb light in a green wavelength region.

20. The image sensor of claim 19, further comprising:
a color filter layer between the semiconductor substrate and the organic photoelectric device, the color filter layer including a blue filter configured to selectively transmit light in a blue wavelength region and a red filter configured to selectively transmit light in a red wavelength region.

21. The image sensor of claim 19, wherein at least two photo-sensing devices of the plurality of first photo-sensing devices and the plurality of second photo-sensing devices are stacked in a vertical direction on the semiconductor substrate.

22. The image sensor of claim 18, wherein
the organic photoelectric device is a green photoelectric device, and
the green photoelectric device configured to selectively absorb light in a green wavelength region, a blue photoelectric device configured to selectively absorb light in a blue wavelength region, and a red photoelectric device configured to selectively absorb light in a red wavelength region are stacked.

23. An electronic device comprising the image sensor of claim 18.

24. A compound for an organic photoelectric device comprising at least one of a compound represented by Chemical Formula 1 and a compound represented by Chemical Formula 2:

[Chemical Formula 1]

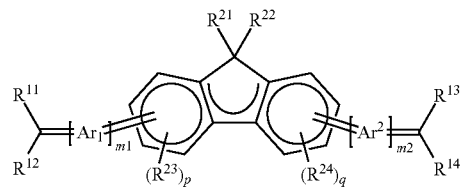

[Chemical Formula 2]

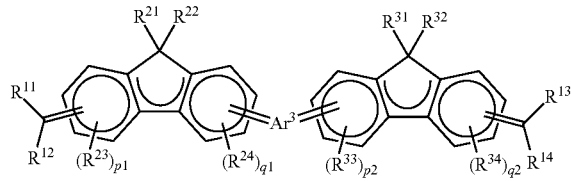

wherein, in Chemical Formulae 1 and 2, each of $R^{11}$ to $R^{14}$ are independently one of hydrogen, a chloro group (—Cl), a bromo group (—Br), a substituted or unsubstituted $C_1$ to $C_{10}$ alkyl group, a cyano group (—CN), and a combination thereof, provided that both $R^{11}$ and $R^{12}$ are not hydrogen and both $R^{13}$ and $R^{14}$ are not hydrogen, each of $R^{21}$, $R^{22}$, $R^{31}$, and $R^{32}$ are independently one of hydrogen, a chloro group (—Cl), a bromo group (—Br), a substituted or unsubstituted $C_1$ to $C_{30}$ alkyl group, and a combination thereof or are optionally linked to provide a spiro structure with a fluorene ring, each of $R^{23}$, $R^{24}$, $R^{33}$, and $R^{34}$ are independently one of hydrogen, a chloro group (—Cl), a bromo group (—Br), a substituted or unsubstituted $C_1$ to $C_{10}$ alkyl group, a cyano group (—CN), and a combination thereof, each of $Ar^1$, and $Ar^2$ are independently one of a substituted or unsubstituted $C_6$ to $C_{30}$ arylene group, a substituted or unsubstituted $C_3$ to $C_{30}$ heteroarylene group that does not include a substituted or unsubstituted thiophene group, and a combination thereof, $Ar^3$ is one of a substituted or unsubstituted $C_6$ to $C_{30}$ arylene group, a substituted or unsubstituted $C_3$ to $C_{30}$ heteroarylene group, and a combination thereof, each of p, p1, p2, q, q1, and q2 are independently an integer ranging from 0 to 3, each of m1 and m2 are 1, wherein the compound represented by Chemical Formula 2 is a compound represented by Chemical Formulae 2-1 or Chemical Formula 2-2,

[Chemical Formula 2-1]

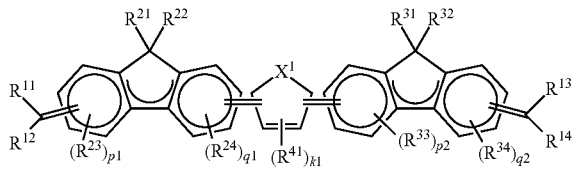

-continued

[Chemical Formula 2-2]

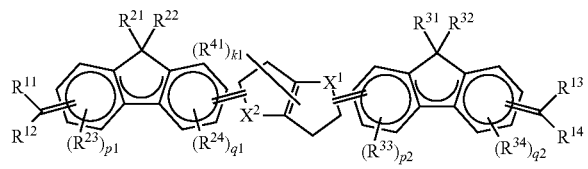

wherein, in Chemical Formulae 2-1 and 2-2, each of $R^{11}$ to $R^{14}$ are independently one of hydrogen, a chloro group (—Cl), a bromo group (—Br), a substituted or unsubstituted $C_1$ to $C_{10}$ alkyl group, a cyano group (—CN), and a combination thereof, provided that both $R^{11}$ and $R^{12}$ are not hydrogen and both $R^{13}$ and $R^{14}$ are not hydrogen, each of $R^{21}$, $R^{22}$, $R^{31}$, and $R^{32}$ are independently one of hydrogen, a chloro group (—Cl), a bromo group (—Br), a substituted or unsubstituted $C_1$ to $C_{30}$ alkyl group, and a combination thereof or are optionally linked to provide a Spiro structure with a fluorene ring, each of $R^{23}$, $R^{24}$, $R^{33}$, $R^{34}$, and $R^{41}$ are independently one of hydrogen, a chloro group (—Cl), a bromo group (—Br), a substituted or unsubstituted $C_1$ to $C_{10}$ alkyl group, a cyano group (—CN), and a combination thereof, each of p1, p2, q1, and q2 are integers ranging from 0 to 3, k1 corresponds to the number of hydrogen in each aromatic ring, and each of $X^1$ and $X^2$ are independently one of S and O.

25. The compound of claim 24, wherein in Chemical Formulae 2-1 and 2-2, at least one of $R^{11}$ to $R^{14}$ is a cyano group (—CN).

26. The compound of claim 24, wherein in Chemical Formulae 2-1 and 2-2, at least two to four of $R^{11}$ to $R^{14}$ are a cyano group (—CN).

27. An image sensor comprising:

an organic photoelectric device including a compound for the organic photoelectric device, the compound for the organic photoelectric device including at least one of a compound represented by Chemical Formula 1 and a compound represented by Chemical Formula 2,

[Chemical Formula 1]

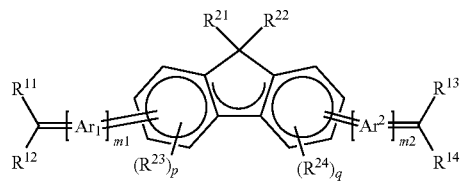

-continued

[Chemical Formula 2]

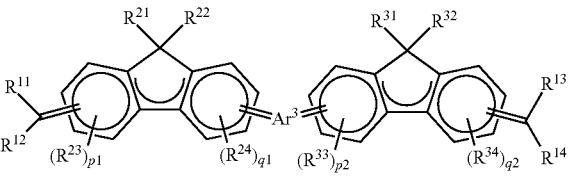

wherein, in Chemical Formulae 1 and 2, each of $R^{11}$ to $R^{14}$ are independently one of hydrogen, a chloro group (—Cl), a bromo group (—Br), a substituted or unsubstituted $C_1$ to $C_{10}$ alkyl group, a cyano group (—CN), and a combination thereof, provided that both $R^{11}$ and $R^{12}$ are not hydrogen and both $R^{13}$ and $R^{14}$ are not hydrogen, each of $R^{21}$, $R^{22}$, $R^{31}$, and $R^{32}$ are independently one of hydrogen, a chloro group (—Cl), a bromo group (—Br), a substituted or unsubstituted $C_1$ to $C_{30}$ alkyl group, and a combination thereof or are optionally linked to provide a spiro structure with a fluorene ring, each of $R^{23}$, $R^{24}$, $R^{33}$, and $R^{34}$ are independently one of hydrogen, a chloro group (—Cl), a bromo group (—Br), a substituted or unsubstituted $C_1$ to $C_{10}$ alkyl group, a cyano group (—CN), and a combination thereof, each of $Ar^1$, and $Ar^2$ are independently one of a substituted or unsubstituted $C_6$ to $C_{30}$ arylene group, a substituted or unsubstituted $C_3$ to $C_{30}$ heteroarylene group that does not include a substituted or unsubstituted thiophene group, and a combination thereof, $Ar^3$ is one of a substituted or unsubstituted $C_6$ to $C_{30}$ arylene group, a substituted or unsubstituted $C_3$ to $C_{30}$ heteroarylene group, and a combination thereof, each of p, p1, p2, q, q1, and q2 are independently an integer ranging from 0 to 3, each of m1 and m2 are 1;

a semiconductor substrate integrated with a plurality of first photo-sensing devices configured to sense light in a blue wavelength region, a plurality of second photo-sensing devices configured to sense light in a red wavelength region, and a plurality of third photo-sensing devices configured to sense light in a green wavelength region, wherein the organic photoelectric device is on the semiconductor substrate and is configured to selectively absorb light in a green wavelength region.

28. The image sensor of claim 27, further comprising:

a color filter layer between the semiconductor substrate and the organic photoelectric device, the color filter including a blue filter configured to selectively transmit light in a blue wavelength region and a red filter configured to selectively transmit light in a red wavelength region.

29. The image sensor of claim 27, wherein at least two photo-sensing devices selected from the first photo-sensing devices, the second photo-sensing devices and the third photo-sensing devices are stacked in a vertical direction on the semiconductor substrate.

* * * * *